United States Patent
Ahmed et al.

(10) Patent No.: US 8,563,305 B2
(45) Date of Patent: Oct. 22, 2013

(54) RAPID GENERATION OF ANTIBODIES

(75) Inventors: Rafi Ahmed, Atlanta, GA (US); Joseph Miller, Atlanta, GA (US); Patrick C. Wilson, Chicago, IL (US); J. Donald Capra, Oklahoma City, OK (US); Jens Wrammert, Decatur, GA (US)

(73) Assignees: Oklahoma Medical Research Foundation, Oklahoma City, OK (US); Emory University, Atlanta, GA (US)

( * ) Notice: Subject to any disclaimer, the term of this patent is extended or adjusted under 35 U.S.C. 154(b) by 194 days.

(21) Appl. No.: 12/433,832

(22) Filed: Apr. 30, 2009

(65) Prior Publication Data

US 2010/0279352 A1 Nov. 4, 2010

(51) Int. Cl.
*C12N 5/06* (2006.01)
*C12N 5/02* (2006.01)

(52) U.S. Cl.
USPC .......................................... 435/326; 435/373

(58) Field of Classification Search
None
See application file for complete search history.

(56) References Cited

FOREIGN PATENT DOCUMENTS

| EP | 1 670 912 B | 5/2008 |
|---|---|---|
| WO | WO2005/042774 | 5/2005 |

OTHER PUBLICATIONS

Babcook et al., PNAS, 1996, v.93,pp. 7843-7848.*
Traggiai et al., Nature Medicine, 2004, v.10, pp. 871-875.*
Harada et al., Br. J. Haemotol, 1996, v.1 pp. 184-191.*
Lanzavecchia A. et al. "Human monoclonal antibodies by immortalization of memory B cells" 2007 Curr. Opin. Biotechnol. 18, 523-528.
Steinitz M. et al. "EB virus-induced B lymphocyte cell lines producing specific antibody" 1977 Nature 269, 420-422.
Kozbor D. et al. "Human hybridomas constructed with antigen-specific Epstein-Barr virus-transformed cell lines" 1982 Proc. Natl Acad. Sci., USA 79, 6651-6655.
Jones PT et al. "Replacing the complementarity-determining regions in a human antibody with those from a mouse" 1986 Nature 321, 522-525.
McCafferty J. et al. "Phage antibodies: filamentous phage displaying antibody variable domains" 1990 Nature 348, 552-554.
Wardemann H. et al. "Predominant autoantibody production by early human B cell precursors" 2003 Science 301, 1374-1377.
Tiller T. et al. "Efficient generation of monoclonal antibodies from single human B cells by single cell RT-PCR and expression vector cloning" 2008 J. Immunol. Methods 329, 112-124.
Mohapatra et al. "Designer monoclonal antibodies as drugs: the state of the art" 2008 Clin. Immunol. 4, 305-307.
Meijer PJ et al. "Isolation of human antibody repertoires with preservation of the natural heavy and light chain pairing" (2006) J. Mol. Biol. 358, 764-772.
Kenneth Smith et al., "Rapid generation of fully human monoclonal antibodies specific to a vaccinating antigen," Nature Protocols, 4:372-384 (2009).
Jens Wrammert et al., "Rapid cloning of high-affinity human monoclonal antibodies against influenza virus," Nature 29:667-671 (2008).

* cited by examiner

*Primary Examiner* — Michail Belyavskyi
(74) *Attorney, Agent, or Firm* — Klarquist Sparkman, LLP

(57) ABSTRACT

High efficient methods for producing an antibody molecule that binds an antigen are described. The methods include obtaining a population of PBMC enriched for $CD19^{high}CD3^{neg}CD20^{low\ to\ neg}CD38^{high}CD27^{high}$ cells from a mammal exposed to an antigen from sample of cells enriched for PBMC. The cells are isolated from a sample obtained at a time that the fraction of PBMC expressing antibody reactive to the antigen is at a high level. Sequences encoding heavy and light chain variable domains are prepared in a manner that allow production of molecules with natural heavy and light chain pairing.

27 Claims, 22 Drawing Sheets

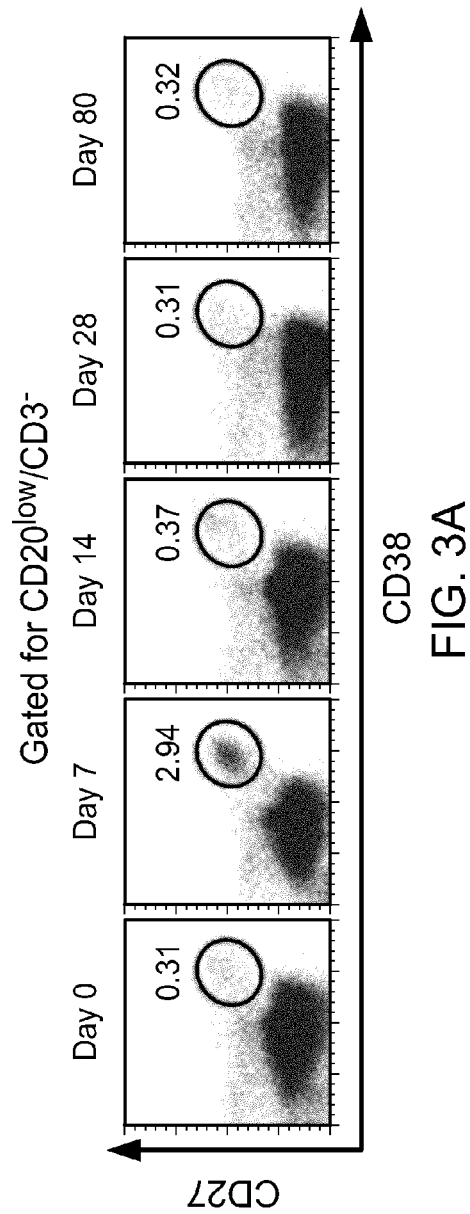
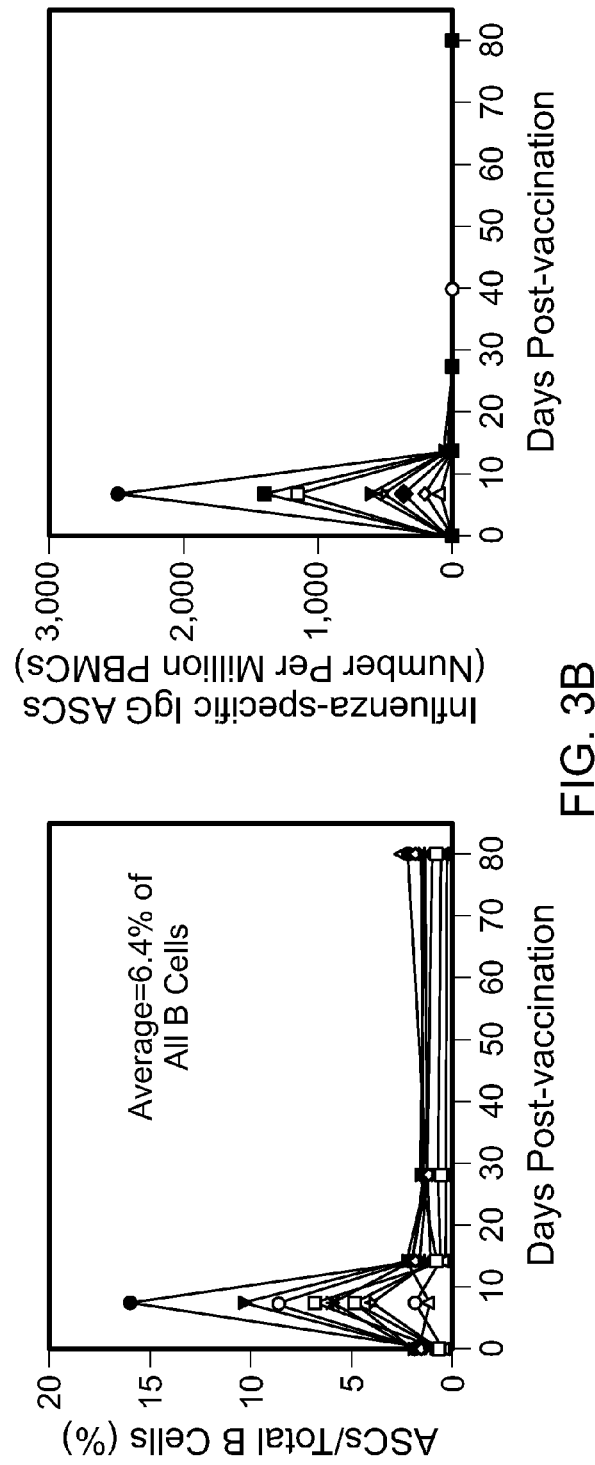
FIG. 3A
FIG. 3B

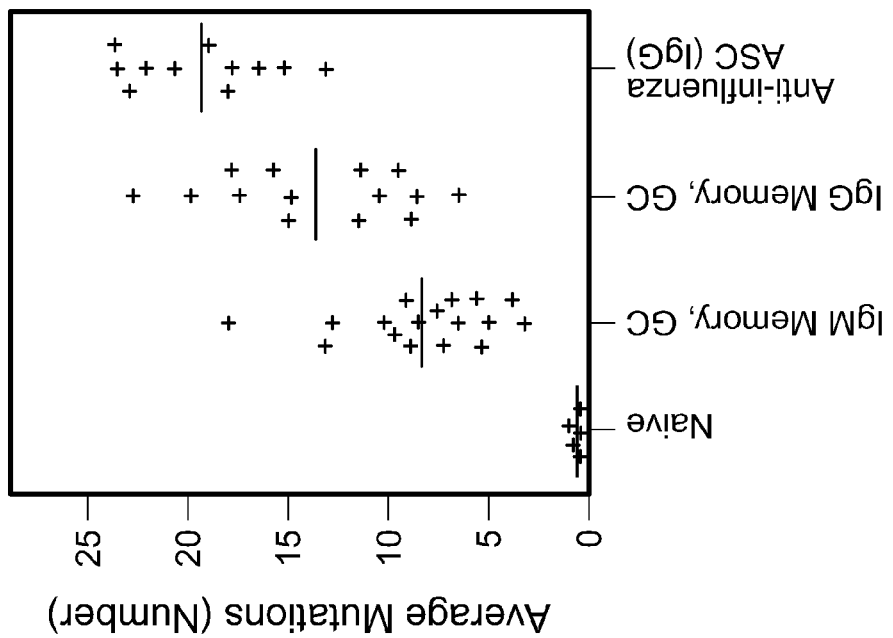
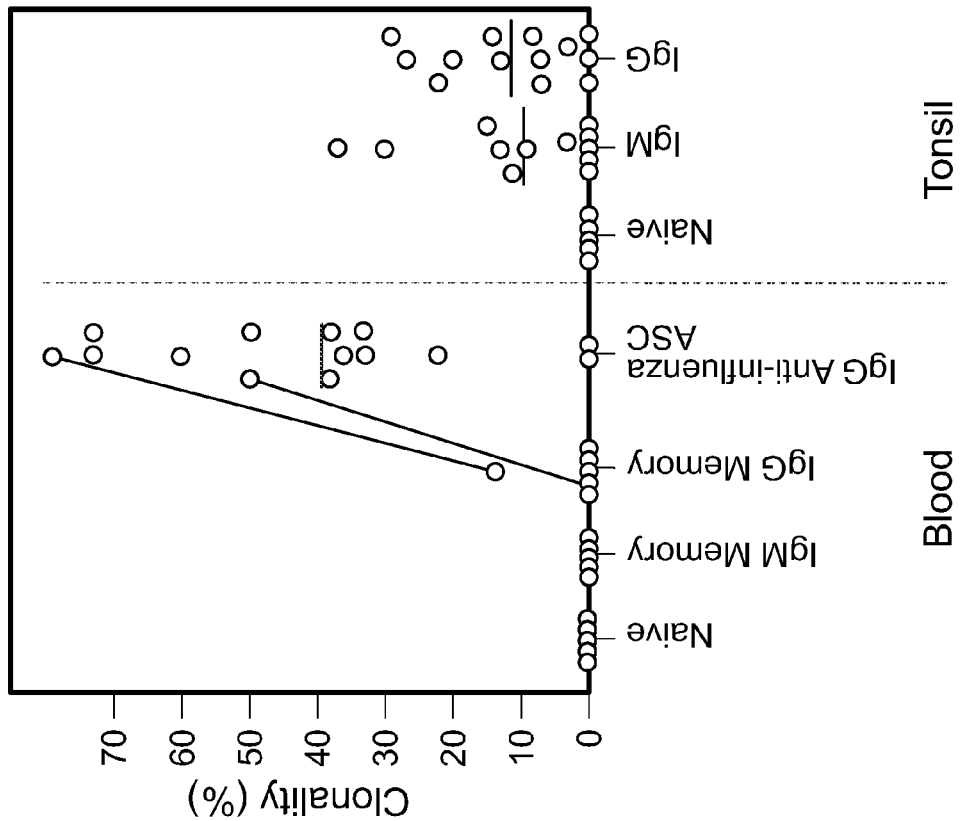
FIG. 4B
FIG. 4A 1988-89  B/Victoria/2/87
1989-91  B/Yamagata/16/88
1991-95  B/Panama/45/90
1995-01  B/Beijing/184/93
2001-02  B/Sichuan/379/99
2002-04  B/Hong Kong/330/2001
2004-06  B/Shanghai/361/2002
2006-07  B/Malaysia/2506/04
FIG. 6A
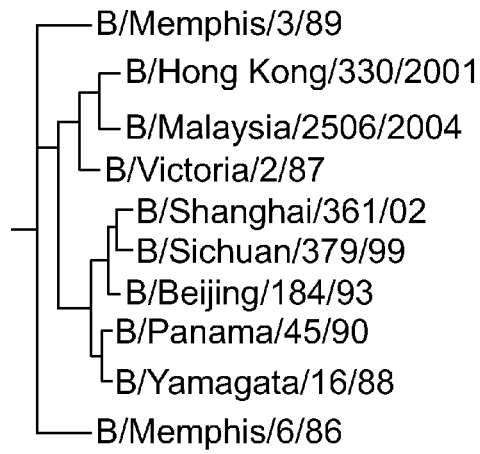
FIG. 6B
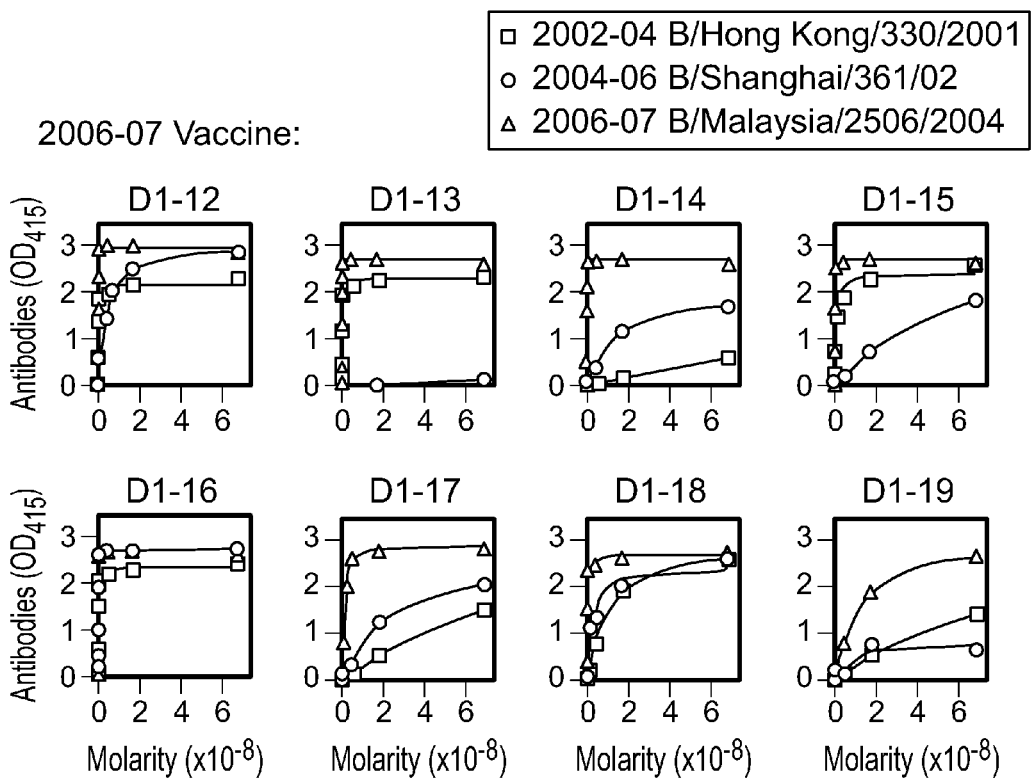
FIG. 6C

| H1N1: A/New Caledonia/20/99 | | | | |
|---|---|---|---|---|
| | Antibody | $K_d$ (M) | HAI | Antigen |
| Donor 1 | D1-1 | $2.70 \times 10^{-10}$ | None | Haemagglutinin |
| | D1-2 (X2)* | $7.33 \times 10^{-10}$ | None | Haemagglutinin |
| | D1-3 (X2)* | $1.55 \times 10^{-9}$ | None | Haemagglutinin |
| | D1-4 | $2.14 \times 10^{-9}$ | None | Haemagglutinin |
| | D1-5 | $2.66 \times 10^{-9}$ | 1 | Haemagglutinin |
| | D1-6 | $3.62 \times 10^{-9}$ | 1 | Haemagglutinin |
| Donor 2 | D2-1 | $2.73 \times 10^{-9}$ | None | 85 Kilodalton (kDa) Band on Western Blot |
| | D2-2 | $5.42 \times 10^{-9}$ | None | 85 kDa Band on Western Blot |
| | D2-3 | $5.20 \times 10^{-9}$ | None | Haemagglutinin |
| Donor 3 | D3-1 | $1.88 \times 10^{-9}$ | None | 85 kDa Band on Western Blot |
| Donor 4 | D4-1 | $4.00 \times 10^{-8}$ | None | 85 kDa Band on Western Blot |
| | D4-2 | $1.65 \times 10^{-8}$ | None | Haemagglutinin |
| Donor 5 | D5-1 | $5.01 \times 10^{-11}$ | None | Multiple Bands on Western Blot |
| | D5-2 | $1.01 \times 10^{-9}$ | None | Denatured Haemagglutinin-1 on Western Blot |
| | D5-3 | $1.78 \times 10^{-8}$ | None | Haemagglutinin |
| | D5-10 | $1.78 \times 10^{-8}$ | None | Multiple Bands on Western Blot |
| H3N2: A/Wisconsin/67/2005(2006/7) or A/California/7/2004 (for Donor 3) | | | | |
| Donor 1 | D1-7 | $7.72 \times 10^{-11}$ | 128 | Haemagglutinin |
| | D1-8 | $2.86 \times 10^{-10}$ | 4 | Haemagglutinin |
| | D1-9 (X4)* | $3.77 \times 10^{-10}$ | 8 | Haemagglutinin |
| | D1-10 | $4.18 \times 10^{-10}$ | 4 | Haemagglutinin |
| | D1-11 | $1.57 \times 10^{-9}$ | None | Nuclear Protein |
| Donor 2 | D2-4 | $3.62 \times 10^{-10}$ | 2 | Haemagglutinin |
| | D2-5 | $8.29 \times 10^{-9}$ | None | Unclear |
| Donor 3 | D3-2 | $3.50 \times 10^{-9}$ | None | Haemagglutinin |
| | D3-3 | $1.56 \times 10^{-8}$ | None | Haemagglutinin |
| | D3-4 | $4.86 \times 10^{-10}$ | 32 | Haemagglutinin |
| Donor 4 | D4-3 | 4.56E-09 | 1 | Haemagglutinin |

FIG. 7

| B Strains: B/Malaysia/2506/2004 or B/Shanghai/361/2004 (Donors 3 and 6) | | | | |
|---|---|---|---|---|
| Donor 1 | D1-12 | $1.93 \times 10^{-10}$ | None | Haemagglutinin |
| | D1-13 | $2.04 \times 10^{-10}$ | 16 | Haemagglutinin |
| | D1-14 (X2)* | $2.43 \times 10^{-10}$ | None | Haemagglutinin |
| | D1-15 | $2.47 \times 10^{-10}$ | 8 | Haemagglutinin |
| | D1-16 | $6.20 \times 10^{-10}$ | None | Haemagglutinin |
| | D1-17 | $6.33 \times 10^{-10}$ | None | Haemagglutinin |
| | D1-18 | $4.74 \times 10^{-10}$ | None | Haemagglutinin |
| | D1-19 | $3.70 \times 10^{-8}$ | None | Matrix Protein on Western Blot |
| Donor 2 | D2-6 | $1.71 \times 10^{-9}$ | None | Unclear |
| | D2-7 | $5.77 \times 10^{-8}$ | None | Matrix Protein on Western Blot |
| | D2-8 | $3.66 \times 10^{-8}$ | None | Haemagglutinin |
| Donor 3 | D3-5 | $1.66 \times 10^{-8}$ | None | Unclear (Low Affinity) |
| | D3-6 | $1.62 \times 10^{-8}$ | None | Denatured Nuclear Protein on Western Blot |
| Donor 4 | D4-4 | $1.71 \times 10^{-8}$ | 1 | Haemagglutinin |
| | D4-5 | $3.28 \times 10^{-8}$ | 4 | Haemagglutinin |
| Donor 5 | D5-5 | $3.78 \times 10^{-8}$ | None | Unclear (Low Affinity) |
| | D5-6 | $1.11 \times 10^{-8}$ | None | Matrix Protein on Western Blot |
| | D5-7 | $1.26 \times 10^{-8}$ | None | Unclear (Low Affinity) |
| | D5-8 | $4.8 \times 10^{-8}$ | None | 85 kDa Band on Western Blot |
| Donor 6 | D6-1 | $5.04 \times 10^{-10}$ | 4 | Haemagglutinin |

* Clonal Expansions with Number of Clones Indicated; Bold; mAbs Tested for Viral Neutralization.

FIG. 7(Cont.)

SEQUENCE LISTING

<160> NUMBER OF SEQ ID NOS: 56

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
acaggtgccc actcccaggt gcag                                        24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
aaggtgtcca gtgtgargtg cag                                             23

<210> SEQ ID NO 3
<211> LENGTH: 27
<212> TYPE: DNA
<213> ORGANISM: Artificial Sequence
<220> FEATURE:
<223> OTHER INFORMATION: Primer

<400> SEQUENCE: 3
cccagatggg tcctgtccca ggtgcag                                         27

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
caaggagtct gttccgaggt gcag                                            24

<210> SEQ ID NO 5
<211> LENGTH: 38
<212> TYPE: DNA
<213> ORGANISM: Artificial Sequence
<220> FEATURE:
<223> OTHER INFORMATION: Primer

<400> SEQUENCE: 5
ctgcaaccgg tgtacattcc gaggtgcagc tggtgcag                             38

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
ctgcaaccgg tgtacattct gaggtgcagc tggtggag                             38

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
ctgcaaccgg tgtacattct gaggtgcagc tgttggag                             38

<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8
ctgcaaccgg tgtacattcc caggtgcagc tgcaggag                             38

<210> SEQ ID NO 9
<211> LENGTH: 40
<212> TYPE: DNA
<213> ORGANISM: Artificial Sequence

```
<220> FEATURE:
<223> OTHER INFORMATION: Primer

<400> SEQUENCE: 9
ctgcaaccgg tgtacattcc caggtgcagc tacagcagtg                    40

<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10
ctgcaaccgg tgtacattcc caggttcagc tggtgcag                      38

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
ctgcaaccgg tgtacattcc caggtccagc tggtacag                      38

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
ctgcaaccgg tgtacattct gaagtgcagc tggtggag                      38

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
ctgcaaccgg tgtacattcc caggtacagc tgcagcag                      38

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
atgaggstcc cygctcagct gctgg                                    25

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
ctcttcctcc tgctactctg gctcccag                                 28
```

```
<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
atttctctgt tgctctggat ctctg                                          25

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
atgacccagw ctccabycwc cctg                                           24

<210> SEQ ID NO 18
<211> LENGTH: 40
<212> TYPE: DNA
<213> ORGANISM: Artificial Sequence
<220> FEATURE:
<223> OTHER INFORMATION: Primer

<400> SEQUENCE: 18
ctgcaaccgg tgtacattct gacatccaga tgacccagtc                          40

<210> SEQ ID NO 19
<211> LENGTH: 46
<212> TYPE: DNA
<213> ORGANISM: Artificial Sequence
<220> FEATURE:
<223> OTHER INFORMATION: Primer

<400> SEQUENCE: 19
ttgtgctgca accggtgtac attcagacat ccagttgacc cagtct                   46

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
ctgcaaccgg tgtacattgt gccatccgga tgacccagtc                          40

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
ctgcaaccgg tgtacatggg gatattgtga tgacccagac                          40

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22
```
ctgcaaccgg tgtacatggg gatattgtga tgactcagtc          40

<210> SEQ ID NO 23
<211> LENGTH: 45
<212> TYPE: DNA
<213> ORGANISM: Artificial Sequence
<220> FEATURE:
<223> OTHER INFORMATION: Primer

<400> SEQUENCE: 23
ttgtgctgca accggtgtac attcagaaat tgtgttgaca cagtc          45

<210> SEQ ID NO 24
<211> LENGTH: 40
<212> TYPE: DNA
<213> ORGANISM: Artificial Sequence
<220> FEATURE:
<223> OTHER INFORMATION: Primer

<400> SEQUENCE: 24
ctgcaaccgg tgtacattca gaaatagtga tgacgcagtc          40

<210> SEQ ID NO 25
<211> LENGTH: 46
<212> TYPE: DNA
<213> ORGANISM: Artificial Sequence
<220> FEATURE:
<223> OTHER INFORMATION: Primer

<400> SEQUENCE: 25
ttgtgctgca accggtgtac attcagaaat tgtgttgacg cagtct          46

<210> SEQ ID NO 26
<211> LENGTH: 40
<212> TYPE: DNA
<213> ORGANISM: Artificial Sequence
<220> FEATURE:
<223> OTHER INFORMATION: Primer

<400> SEQUENCE: 26
ctgcaaccgg tgtacattcg gacatcgtga tgacccagtc          40

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
ggtcctgggc ccagtctgtg ctg          23

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
ggtcctgggc ccagtctgcc ctg          23

<210> SEQ ID NO 29
<211> LENGTH: 23
<212> TYPE: DNA
<213> ORGANISM: Artificial Sequence

```
<220> FEATURE:
<223> OTHER INFORMATION: Primer

<400> SEQUENCE: 29
gctctgtgac ctcctatgag ctg                                         23

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
ggtctctctc scagcytgtg ctg                                         23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
gttcttgggc caattttatg ctg                                         23

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
ggtccaattc ycaggctgtg gtg                                         23

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
gagtggattc tcagactgtg gtg                                         23

<210> SEQ ID NO 34
<211> LENGTH: 38
<212> TYPE: DNA
<213> ORGANISM: Artificial Sequence
<220> FEATURE:
<223> OTHER INFORMATION: Primer

<400> SEQUENCE: 34
ctgctaccgg ttcctgggcc cagtctgtgc tgackcag                         38

<210> SEQ ID NO 35
<211> LENGTH: 38
<212> TYPE: DNA
<213> ORGANISM: Artificial Sequence
<220> FEATURE:
<223> OTHER INFORMATION: Primer

<400> SEQUENCE: 35
ctgctaccgg ttcctgggcc cagtctgccc tgactcag                         38
```

```
<210> SEQ ID NO 36
<211> LENGTH: 38
<212> TYPE: DNA
<213> ORGANISM: Artificial Sequence
<220> FEATURE:
<223> OTHER INFORMATION: Primer

<400> SEQUENCE: 36
ctgctaccgg ttctgtgacc tcctatgagc tgacwcag                    38

<210> SEQ ID NO 37
<211> LENGTH: 37
<212> TYPE: DNA
<213> ORGANISM: Artificial Sequence
<220> FEATURE:
<223> OTHER INFORMATION: Primer

<400> SEQUENCE: 37
ctgctaccgg ttctctctcs cagcytgtgc tgactca                     37

<210> SEQ ID NO 38
<211> LENGTH: 38
<212> TYPE: DNA
<213> ORGANISM: Artificial Sequence
<220> FEATURE:
<223> OTHER INFORMATION: Primer

<400> SEQUENCE: 38
ctgctaccgg ttcttgggcc aattttatgc tgactcag                    38

<210> SEQ ID NO 39
<211> LENGTH: 38
<212> TYPE: DNA
<213> ORGANISM: Artificial Sequence
<220> FEATURE:
<223> OTHER INFORMATION: Primer

<400> SEQUENCE: 39
ctgctaccgg ttccaattcy cagrctgtgg tgacycag                    38

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
gcttcgttag aacgcggcta c                                      21

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
sargtgcagc tcgtggag                                          18

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
```

```
gaggtgcagc tgttggag                                        18

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
tcttgtccac cttggtgttg ct                                   22

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
gggaattctc acaggagacg a                                    21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ggaattctca caggagacga                                      20

<210> SEQ ID NO 46
<211> LENGTH: 25
<212> TYPE: DNA
<213> ORGANISM: Artificial Sequence
<220> FEATURE:
<223> OTHER INFORMATION: Primer

<400> SEQUENCE: 46
agtagtcctt gaccaggcag cccag                                25

<210> SEQ ID NO 47
<211> LENGTH: 32
<212> TYPE: DNA
<213> ORGANISM: Artificial Sequence
<220> FEATURE:
<223> OTHER INFORMATION: Primer

<400> SEQUENCE: 47
tgcgaagtcg acgctgagga gacggtgacc ag                        32

<210> SEQ ID NO 48
<211> LENGTH: 34
<212> TYPE: DNA
<213> ORGANISM: Artificial Sequence
<220> FEATURE:
<223> OTHER INFORMATION: Primer

<400> SEQUENCE: 48
tgcgaagtcg acgctgaaga gacggtgacc attg                      34

<210> SEQ ID NO 49
<211> LENGTH: 33
<212> TYPE: DNA
<213> ORGANISM: Artificial Sequence
```

```
<220> FEATURE:
<223> OTHER INFORMATION: Primer

<400> SEQUENCE: 49
tgcgaagtcg acgctgagga gacggtgacc gtg                              33

<210> SEQ ID NO 50
<211> LENGTH: 24
<212> TYPE: DNA
<213> ORGANISM: Artificial Sequence
<220> FEATURE:
<223> OTHER INFORMATION: Primer

<400> SEQUENCE: 50
gtttctcgta gtctgctttg ctca                                        24

<210> SEQ ID NO 51
<211> LENGTH: 22
<212> TYPE: DNA
<213> ORGANISM: Artificial Sequence
<220> FEATURE:
<223> OTHER INFORMATION: Primer

<400> SEQUENCE: 51
gtgctgtcct tgctgtcctg ct                                          22

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
gccaccgtac gtttgatytc caccttggtc                                  30

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
gccaccgtac gtttgatatc cactttggtc                                  30

<210> SEQ ID NO 54
<211> LENGTH: 30
<212> TYPE: DNA
<213> ORGANISM: Artificial Sequence
<220> FEATURE:
<223> OTHER INFORMATION: Primer

<400> SEQUENCE: 54
gccaccgtac gtttaatctc cagtcgtgtc                                  30
```

```
<210> SEQ ID NO 55
<211> LENGTH: 24
<212> TYPE: DNA
<213> ORGANISM: Artificial Sequence
<220> FEATURE:
<223> OTHER INFORMATION: Primer

<400> SEQUENCE: 55
caccagtgtg gccttgttgg cttg                                            24

<210> SEQ ID NO 56
<211> LENGTH: 28
<212> TYPE: DNA
<213> ORGANISM: Artificial Sequence
<220> FEATURE:
<223> OTHER INFORMATION: Primer

<400> SEQUENCE: 56
ctcctcactc gagggyggga acagagtg                                        28
```

RAPID GENERATION OF ANTIBODIES

GOVERNMENT SUPPORT

This invention was made with government support under grant no. AI057266 awarded by the National Institutes of Health. The government has certain rights in the invention.

BACKGROUND

Human antibodies can be produced by several methods, including immortalization of B cells with Epstein-Barr virus, and the production of B-cell hybridomas, humanization of antibodies from other species, using phage display libraries or generating antibodies recombinantly from isolated single B cells (see, e.g., Lanzavecchia et al. 2007 Curr. Opin. Biotechnol. 18, 523-528; Steinitz et al. 1977 Nature 269, 420-422; Kozbor 1982 Proc. Natl Acad. Sci. USA 79, 6651-6655; Jones et al. 1986 Nature 321, 522-525; McCafferty et al. 1990 Nature 348, 552-554; Wardemann et al. 2003 Science 301, 1374-1377; Tiller et al. 2008 J. Immunol. Methods 329, 112-124; Mohapatra et al. 2008 Clin. Immunol. 4, 305-307. In methods requiring immortalized B-cell lines, the extensive subcloning and overall shotgun approach can limit the number of useful antibodies that can be produced even over extensive periods of time. Some phage display and related platforms can be very time-consuming and can sometimes yield relatively few candidate antibodies, a significant portion of which are low affinity. If a technology for producing fully human antibodies uses heavy and light chain variable genes that are randomly paired, the antibodies so produced can elicit an unwanted immune response. There are methods that reportedly produce cognate heavy and light chain pairs, but certain of these methods entail pooling nucleic acids encoding cognate pairs followed by subsequent selection from pooled clones (see, e.g., Meijer et al. (2006) J. Mol. Biol. 358, 764-722; EP 2 670 912 B) The mAbs generated by in vitro methods or in other species do not provide a true evaluation of the epitope specificities that humans generate in vivo, limiting the use of these techniques for applications such as epitope discovery and vaccine development or evaluation. These same applications have been hindered by technologies using immortalized B-cell lines because of the relatively few specific antibodies isolated that can be generated. Finally, for potential therapeutic applications, the Fab that is produced by phage display libraries or in other species (mice) must be cloned and fused to a human Fc backbone and expressed in a human cell line.

Influenza, commonly known as the flu, is an infectious disease of birds and mammals caused by an RNA virus of the family Orthomyxoviridae (the influenza viruses). In humans, common symptoms of influenza infection are fever, nausea, vomiting, sore throat, muscle pains, severe headache, coughing, and weakness and fatigue. In more serious cases, influenza causes pneumonia, which can be fatal, particularly in young children and the elderly. Sometimes confused with the common cold, influenza is a much more severe disease and is caused by a different type of virus.

Typically, influenza is transmitted from infected mammals through the air by coughs or sneezes, creating aerosols containing the virus, and from infected birds through their droppings. Influenza can also be transmitted by saliva, nasal secretions, feces and blood. Infections occur through contact with these bodily fluids or with contaminated surfaces. Flu viruses can remain infectious for about one week at human body temperature, over 30 days at 0° C. (32° F.), and indefinitely at very low temperatures. The virus can be inactivated easily by disinfectants and detergents. Flu spreads around the world in seasonal epidemics, killing millions of people in pandemic years and hundreds of thousands in non-pandemic years. Three influenza pandemics occurred in the 20th century—each following a major genetic change in the virus—and killed tens of millions of people. Often, these pandemics result from the spread of a flu virus between different animal species.

Vaccinations against influenza are most now commonly given in most industrialized countries, although limited quantities often mean that only high risk groups (children and the elderly) are targeted. The most common human vaccine is the trivalent flu vaccine that contains purified and inactivated material from three viral strains. Typically this vaccine includes material from two influenza A virus subtypes and one influenza B virus strain.

However, there are shortcomings to the vaccine approach. For example, a vaccine formulated for one year may be ineffective in the following year as the influenza virus changes rapidly and different strains become dominant. Moreover, the time needed to produce a new vaccine in response to an emerging strain of influenza is on the order of about six months, which is far to slow to intervene in the early stages of an outbreak. It is also possible to get infected just before vaccination and get sick with the very strain that the vaccine is supposed to prevent, as the vaccine takes about two weeks to become effective. Finally, perhaps the most daunting issue with vaccine is the potential for dangerous side-effects stemming from severe allergic reaction to either the virus material itself, or residues from the hen eggs used to grow the influenza. Thus, and improved preventative approaches for influenza, as well as many other infectious and non-infectious disease states, are needed.

SUMMARY

An example of the overall method for rapidly producing human antibodies is depicted in FIG. 1. First antibody-secreting cells (ASCs) are isolated from whole blood that is collected from a subject at a selected time after exposure to an immunogen. PBMCs are isolated using a standard lymphocyte separation protocol. The frequency of antigen-specific ASCs is optionally analyzed using a standard ELISpot protocol (see Box 1). This optional assay enumerates the number of IgG-producing ASCs, as well as antigen-specific ASCs. The percentage of antigen-specific, IgG producing ASCs is a useful measure of the donor's production of antibodies to a selected antigen and therefore the approximate quantity of high-affinity antibodies produced. The cells are then sorted by flow cytometry. First, the live cell gate, including larger blasting cells, is set using forward versus side scatter. The ASCs are bulk sorted by first gating on CD19high/CD20low to negative/CD3negative and then on CD27high/CD38high cells as shown in FIG. 2. The appropriate IgG, IgM and IgD gates are set to obtain IgG-producing ASCs, although it is also possible to use this method to isolate IgM-producing ASCs as well. Finally, the purified ASCs are single cell sorted into single cell PCR plates loaded with catch buffer containing RNase inhibitor.

Using both RT-PCR and nested PCR, the antibody genes in each cell are amplified on a per cell basis. The RT-PCR is accomplished using a cocktail of nine primers, designed to cover all of the families of variable (V) genes possible (e.g., the primers of Table 1). The nested PCR is performed to amplify the DNA enough to obtain sequences of the heavy and light chain V genes. This is necessary for the cloning PCR. In this step, highly specific primers for each V gene family are used to amplify the DNA for cloning. The 'cloning PCR' primers are designed both to incorporate the cloning restriction sites and to place the VDJ heavy or VJ light chain genes in frame with the signal peptide sequences and constant region genes within the respective cloning vectors. Cloning sites were incorporated into the vectors that are specific for the particular heavy or light chain vectors to allow proper, in-frame incorporation of the variable gene inserts. The inserts and vectors are then digested and purified for cloning.

The heavy and light chain DNA from each single cell is then cloned into separate vectors and transformed. At least four colonies from the transformation are grown, miniprepped and sequenced. The sequences from each colony are compared and the colony most closely matching the consensus is then chosen for further amplification to maxi scale. Transiently transfected human kidney epithelial cells (the HEK293 cell line19) are used to produce the antibody. Polyethyleneimine-based transfection is used with equimolar amounts of heavy and light chain vector according to standard protocols. The cells are allowed to produce antibody for 5 days. The transfection media containing the hmAbs are then purified using protein A agarose beads and concentrated using commercial protein concentrators. During the final stage, the hmAbs are analyzed for concentration, purity and reactivity.

Aspects of the method that make the isolation of specific antibodies rapid and efficient include: selection of an appropriate subpopulation of PBMC; use of a biological sample obtained at the appropriate time after exposure to the immunogen (e.g., 6-9 days after a second exposure or 13-15 days after a first exposure; avoidance of pooling of heavy and light chain clones whether the heavy and light chains are present in the same nucleic acid (i.e., linked heavy and light chain coding sequences) or different nucleic acid molecules (i.e., where heavy and light chain coding sequences are not present in the same nucleic acid molecule).

Described herein is a method for producing an antibody molecule (e.g., a complete antibody or a portion thereof (e.g., a Fab, scFv, single-chain Fv or any peptide that includes a heavy chain variable domain and a light chain variable domain or a pair of peptide one of which contains a heavy chain variable domain and the other of which contains a light chain variable domain) that binds an antigen (or immunogen), the method comprising:

(a) providing a biological sample comprising antibody producing cells obtained from a mammal (e.g., a human) that has been exposed to an antigen, wherein the sample is obtained from the mammal after exposure of the mammal to the antigen;

(b) prepare a sample of cells enriched for PBMC from the biological sample;

(c) obtaining a population of cells enriched for $CD19^{high}CD3^{neg}CD20^{low\ to\ neg}CD38^{high}CD27^{high}$ cells from sample of cells enriched for PBMC;

(d) selecting a cell from the population of cells enriched for $CD19^{high}CD3^{neg}CD20^{low\ to\ neg}CD38^{high}CD27^{high}$ cells;

(e) isolating from the selected cell or progeny of the selected cell, a nucleic acid molecule encoding at least a portion of an antibody light chain expressed by the cell, wherein the portion comprises the variable domain and a nucleic acid molecule encoding at least a portion of an antibody heavy chain expressed by the cell, wherein the portion comprises the variable domain (In some cases the nucleic acid molecule that encodes the antibody light chain does not encode the antibody heavy chain.);

(f) transforming a recombinant cell with the nucleic acid sequence encoding at least a portion an antibody light chain comprising the light chain variable domain and a nucleic acid sequence encoding at least a portion of an antibody heavy chain comprising the heavy chain variable domain, wherein the light chain variable domain and the heavy chain variable were paired in the selected cell; and (g) culturing the recombinant cell to produce an antibody molecule the binds the antigen.

Also described is a method for obtaining a composition comprising a first nucleic acid molecule encoding a single light chain variable domain and a second nucleic acid molecule encoding a single heavy chain variable domain wherein the two variable domains were paired in an antibody generated by a mammal and wherein the composition is free of nucleic acid molecules encoding additional heavy or light chain variable domains, the method comprising:

(a) providing a biological sample comprising antibody producing cells obtained from a mammal (e.g., a human) that has been exposed to an antigen, wherein the sample is obtained from the mammal after exposure of the mammal to the antigen;

(b) prepare a sample of cells enriched for PBMC from the biological sample;

(c) obtaining a population of cells enriched for $CD19^{high}CD3^{neg}CD20^{low\ to\ neg}CD38^{high}CD27^{high}$ cells from sample of cells enriched for PBMC;

(d) selecting a cell from the population of cells enriched for $CD19^{high}CD3^{neg}CD20^{low\ to\ neg}CD38^{high}CD27^{high}$ cells;

(e) isolating from the selected cell or progeny of the selected cell, a nucleic acid molecule encoding at least a portion of an antibody light chain expressed by the cell, wherein the portion comprises the variable domain and a nucleic acid molecule encoding at least a portion of an antibody heavy chain expressed by the cell, wherein the portion comprises the variable domain. The nucleic acid molecules (or portions thereof encoding variable domains) in the composition can inserted (separately or together) into expression vectors and used to transform a cell that permits expression of a polypeptide or polypeptides expressing the variable domains. Preferably the method does not entail pooling of nucleic acid molecules that encode different light chain variable domains or different heavy chain variable domains. In other words, in certain embodiments, two nucleic acid molecules encoding two different light chain variable domains (or heavy chain variable domains) are not present in the same cell or composition.

In various embodiments of the methods: the mammal has been exposed to the antigen at least twice and the biological sample is collected from the mammal 3-10 (preferably 6-8, preferably 7 days) after the second (or subsequent) exposure to the antigen; the mammal has been exposed only once to the antigen and the biological sample is collected from the mammal 10-18 (preferably 12-16, preferably 14 days after the single exposure to the antigen; the exposure to the antigen comprises immunization of the mammal with the antigen; the exposure to the antigen comprises accidental or deliberate infection of the mammal with an infectious agent comprising the antigen; the antigen is a self-antigen; antigen is tumor antigen; step (c) comprises first enriching for $CD19^{high}CD3^{neg}CD20^{low\ to\ neg}$ cells and then enriching for $CD38^{high}CD27^{high}$ cells; step (c) further comprises enriching for $IgM^{neg}, IgD^{neg}, IgG^{pos}$ cells; step (d) comprises single cell sorting; the method further comprises immunizing the mammal with a composition comprising the antigen prior to step (a); the infectious agent is a virus (e.g., an influenza virus, a herpes virus, a lenti virus, a pox virus, or a corona virus); at least 30% (e.g., 40%, 50%, 60%, 70% or even 80%) of the cells in the population of cells enriched for $CD19^{high}CD3^{neg}CD20^{low\ to\ neg}CD38^{high}CD27^{high}$ express an antibody that binds to the antigen.

Antigens Eliciting Antibodies

The methods described can be used to generate human antibodies as well as antibodies from any mammal (e.g., horse, dog, cow, mouse, rate, rabbit) exposed to an antigen either by deliberated vaccination or other exposure to an immunogen. For example a subject can be exposed to an immunogen by infection with a infectious agent or exposure to a non-self antigen such as an antigen expressed by a cancer cell. Antibodies to autoantigens can also be prepared.

The methods are particularly useful for generating antibodies to various types of influenza virus. Influenza viruses are RNA viruses of the family Orthomyxoviridae, which comprises: Influenzaviruses, Isavirus and Thogotovirus. There are three types of influenza virus: Influenzavirus A, Influenzavirus B or Influenzavirus C. Influenza A and C infect multiple species, while influenza B almost exclusively infects humans. The type A viruses are the most virulent human pathogens among the three influenza types, and cause the most severe disease. The Influenza A virus can be subdivided into different serotypes based on the antibody response to these viruses. The serotypes that have been confirmed in humans, ordered by the number of known human pandemic deaths, are: H1N1 caused "Spanish Flu"; H2N2 (caused "Asian Flu"); H3N2 (caused "Hong Kong Flu"); H7N7; H1N2 (endemic in humans and pigs; H9N2; H7N2; H7N3; and H10N7.

Influenza B virus is almost exclusively a human pathogen, and is less common than influenza A. The only other animal known to be susceptible to influenza B infection is the seal. This type of influenza mutates at a rate 2-3 times lower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur. The influenza C virus infects humans and pigs, and can cause severe illness and local epidemics. However, influenza C is less common than the other types and usually seems to cause mild disease in children.

In addition to influenza, a variety of other viruses may be used to generate antibodies, and subsequently be diagnosed or treated, by antibodies. The viruses include Abelson murine leukemia virus, Retroviridae
  Adelaide River virus, Rhabdoviridae
  Adeno-associated virus 1, Parvoviridae
  Adeno-associated virus 2, Parvoviridae
  Adeno-associated virus 3, Parvoviridae
  Adeno-associated virus 4, Parvoviridae
  Adeno-associated virus 5, Parvoviridae
  African green monkey cytomegalovirus, Herpesviridae
  African green monkey HHV-like virus, Herpesviridae
  African green monkey polyomavirus, Papovaviridae
  African horse sickness viruses 1 to 10, Reoviridae
  African swine fever virus, African swine fever-like viruses
  Aleutian disease virus, Parvoviridae
  Aleutian mink disease virus, Parvoviridae
  American ground squirrel herpesvirus, Herpesviridae
  Baboon herpesvirus, Herpesviridae
  Baboon polyomavirus 2, Papovaviridae
  Bovine adeno-associated virus, Parvoviridae
  Bovine adenoviruses 1 to 9, Adenoviridae
  Bovine astrovirus 1, Astroviridae
  Bovine astrovirus 2, Astroviridae
  Bovine coronavirus, Coronaviridae
  Bovine diarrhea virus, Flaviviridae
  Bovine encephalitis herpesvirus, Herpesviridae
  Bovine enteric calicivirus, Caliciviridae
  Bovine enterovirus 1, Picornaviridae
  Bovine enterovirus 2, Picornaviridae
  Bovine ephemeral fever virus, Rhabdoviridae
  Bovine herpesvirus 1, Herpesviridae
  Bovine herpesvirus 2, Herpesviridae
  Bovine herpesvirus 4, Herpesviridae
  Bovine herpesvirus 5, Herpesviridae
  Bovine immunodeficiency virus, Retroviridae
  Bovine leukemia virus, Retroviridae
  Bovine mamillitis virus, Herpesviridae
  Bovine papillomavirus 1, Papovaviridae
  Bovine papillomavirus 2, Papovaviridae
  Bovine papillomavirus 4, Papovaviridae
  Bovine papular stomatitis virus, Poxviridae
  Bovine parainfluenza virus 3, Paramyxoviridae
  Bovine parvovirus, Parvoviridae
  Bovine polyomavirus, Papovaviridae.
  Bovine respiratory syncytial virus, Paramyxoviridae
  Bovine rhinovirus 1, Picornaviridae
  Bovine rhinovirus 2, Picornaviridae
  Bovine rhinovirus 3, Picornaviridae
  Bovine syncytial virus, Retroviridae
  California encephalitis virus, Bunyaviridae
  California harbor sealpox virus, Poxviridae
  Canine adeno-associated virus, Parvoviridae
  Canine adenovirus 1, Adenoviridae
  Canine adenovirus 2, Adenoviridae
  Canine calicivirus, Caliciviridae
  Canine coronavirus, Coronaviridae
  Canine distemper virus, Paramyxoviridae
  Canine herpesvirus, Herpesviridae
  Canine minute virus, Paruoviridae
  Canine oral papillomavirus, Papovaviridae
  Canine parvovirus, Parvoviridae
  Chicken anemia virus, Circoviridae
  Chicken parvovirus, Paruoviridae
  Chimpanzee herpesvirus, Herpesviridae
  Cottontail herpesvirus, Herpesviridae
  Cottontail rabbit papillomavirus, Papovaviridae
  Cowpox virus, Poxviridae
  Deer fibroma virus, Papovaviridae
  Deer papillomavirus, Papovaviridae
  Elephant loxondontal herpesvirus, Herpesviridae
  Elephant papillomavirus, Papovaviridae
  Elephantid herpesvirus, Herpesviridae
  Epstein-Barr virus, Herpesviridae
  Equid herpesvirus 1, Herpesviridae
  Equid herpesvirus 2, Herpesviridae
  Equid herpesvirus 3, Nerpesviridae
  Equid herpesvirus 4, Herpesviridae
  Equid herpesvirus 5, Herpesviridae
  Equid herpesvirus 6, Herpesviridae
  Equid herpesvirus 7, Herpesviridae
  Equid herpesvirus 8, Herpesviridae
  Equine abortion herpesvirus, Herpesviridae
  Equine adeno-associated virus, Parvoviridae
  Equine adenovirus 1, Adenoviridae
  Equine arteritis virus, Arterivirus
  Equine cytomegalovirus, Herpesviridae
  Equine encephalosis viruses 1 to 7, Reoviridae Equine herpesvirus 1, Herpesviridae
Equine herpesvirus 3, Herpesviridae
Equine herpesvirus 4, Herpesviridae
Equine herpesvirus 5, Herpesviridae
Equine infectious anemia virus, Retroviridae
Equine papillomavirus, Papovaviridae
Equine rhinopneumonitis virus, Herpesviridae
Equine rhinovirus 1, Picornaviridae
Equine rhinovirus 2, Picornaviridae
Equine rhinovirus 3, Picornaviridae
European bat virus 1, Rhabdoviridae
European bat virus 2, Rhabdoviridae
European brown hare syndrome virus, Caliciviridae
European elk papillomavirus, Papovaviridae
European ground squirrel cytomegalovirus, Herpesviridae
European hedgehog herpesvirus, Herpesviridae
Feline calicivirus, Caliciviridae
Feline herpesvirus 1, Herpesviridae
Feline immunodeficiency virus, Retroviridae
Feline infectious peritonitis virus, Coronaviridae
Feline leukemia virus, Retroviridae
Feline parlleukopenia virus, Parvoviridae
Feline parvovirus, Parvoviridae
Feline syncytial virus, Retroviridae
Feline viral rhinotracheitis virus, Herpesviridae
Field mouse herpesvirus, Herpesviridae
Foot-and-mouth disease virus A, Picornaviridae
Foot-and-mouth disease virus ASIA 1, Picornaviridae
Foot-and-mouth disease virus C, Picornaviridae
Foot-and-mouth disease virus O, Picornaviridae
Foot-and-mouth disease virus SAT 1, Picornaviridae
Foot-and-mouth disease virus SAT 2, Picornaviridae
Foot-and-mouth disease virus SAT 3, Picornaviridae
Goat herpesvirus, Herpesviridae
Goatpox virus, Poxviridae
Ground squirrel hepatitis B virus, Hepadnaviridae
Group A rotaviruses, Reoviridae
Group B rotaviruses, Reoviridae
Group C rotaviruses, Reoviridae
Group D rotaviruses, Reoviridae
Group E rotaviruses, Reoviridae
Group F rotaviruses, Reoviridae
Guinea pig cytomegalovirus, Herpesviridae
Guinea pig herpesvirus 1, Herpesviridae
Guinea pig herpesvirus 3, Herpesviridae
Guinea pig t, vpe C oncovirus, Retroviridae
Hamster herpesvirus, Herpesviridae
Hamster polyomavirus, Papovaviridae
Hantaan virus, Bunyaviridae
Harbor seal herpesvirus, Herpesviridae
Hare fibroma virus, Poxviridae
Hepatitis A virus, Picornaviridae
Hepatitis B virus, Hepadnaviridae
Hepatitis C virus, Flaviviridae
Herpesvirus M, Herpesviridae
Herpesvirus papio, Herpesviridae
Herpesvirus platyrrhinae type, Herpesviridae
Herpesvirus pottos, Herpesviridae
Herpesvirus saimiri 2, Herpesviridae
Herpesvirus salmonis, Herpesviridae
Herpesvirus sanguinus, Herpesviridae
Herpesvirus scophthalmus, Herpesviridae
Herpesvirus sylvilagus, Herpesviridae
Herpesvirus T, Herpesviridae
Herpesvirus tarnarinus, Herpesviridae
Hog cholera virus, Flaviviridae
Herpes simiae virus, Herpesviridae
Herpes simplex virus 1, Herpesviridae
Herpes simplex virus 2, Herpesviridae
Herpes virus B, Herpesviridae
Herpesvirus aotus 1, Herpesviridae
Herpesvirus aotus 3, Herpesviridae
Herpesvirus ateles strain 73, Herpesviridae
Herpesvirus cuniculi, Herpesviridae
Herpesvirus cyclopsis, Herpesviridae
Human adenoviruses 1 to 47, Adenoviridae
Human astrovirus 1, Astroviridae
Human astrovirus 2, Astroviridae
Human astrovirus 3, Astroviridae
Human astrovirus 4, Astroviridae
Human astrovirus 5, Astroviridae
Human calicivirus, Caliciviridae
Human caliciviruses, Caliciviridae
Human coronavirus 229E, Coronaviridae
Human coronavirus OC43, Coronaviridae
Human coxsackievirus A 1 to 22, Picornaviridae
Human coxsackievirus A 24, Picornaviridae
Human coxsackievirus B 1 to 6, Picornaviridae
Human cytomegalovirus, Herpesviridae
Human echovirus 1 to 7, Picornaviridae
Human echovirus 11 to 27, Picornaviridae
Human echovirus 29 to 33, Picornaviridae
Human echovirus 9, Picornaviridae
Human enterovirus 68 to 71, Picornaviridae
Human foamy virus, Retroviridae
Human herpesvirus 1, Herpesviridae
Human herpesvirus 2, Herpesviridae
Human herpesvirus 3, Herpesviridae
Human herpesvirus 4, Nerpesviridae
Human herpesvirus 5, Herpesviridae
Human herpesvirus 6, Herpesviridae
Human herpesvirus 7, Herpesviridae
Human immunodeficiency virus 1, Retroviridae
Human immunodeficiency virus 2, Retroviridae
Human papillomavirus 11, Papovaviridae
Human papillomavirus 16, Papovaviridae
Human papillomavirus 18, Papovaviridae
Human papillomavirus 31, Papovaviridae
Human papillomavirus 33, Papovaviridae
Human papillomavirus 5, Papovaviridae
Human papillomavirus 6b, Papovaviridae
Human papillomavirus 8, Papovaviridae
Human papillomavirus 1a, Papovaviridae
Human parainfluenza virus 1, Paramyxoviridae
Human parainfluenza virus 2, Paramyxoviridae
Human parainfluenza virus 3, Paramyxoviridae
Human parainfluenza virus 4a, Paramyxoviridae
Human parainfluenza virus 4b, Paramyxoviridae
Human poliovirus 1, Picornaviridae
Human poliovirus 2, Picornaviridae
Human poliovirus 3, Picornaviridae
Human respiratory syncytial virus, Paramyxoviridae
Human rhinovirus 1 to 100, Picornaviridae
Human rhinovirus 1A, Picornaviridae
Human spumavirus, Retroviridae
Human T-lymphotropic virus 1, Retroviridae
Human T-lymphotropic virus 2, Retroviridae
Jaagsiekte virus, Retroviridae
Japanese encephalitis virus, Flaviviridae
JC virus, Papovaviridae
Kirsten murine sarcoma virus, Retroviridae
Lagos bat virus, Rhabdoviridae
Lymphocytic choriomeningitis virus, Arenaviridae
Mice minute virus, Parvoviridae Mice pneumotropic virus, Papovaviridae
Moloney murine sarcoma virus, Retroviridae
Moloney virus, Retroviridae
Monkeypox virus, Poxviridae
Mouse cytomegalovirus 1, Herpesviridae
Mouse Elberfield virus, Picornaviridae
Mouse herpesvirus strain 68, Herpesviridae
Mouse mammary tumor virus, Retroviridae
Mouse thymic herpesvirus, Herpesviridae
Mule deerpox virus, Poxviridae
Murine adenovirus 2, Adenoviridae
Z murine adenovirus 1, Adenoviridae
Murine hepatitis virus, Coronaviridae
Murine herpesvirus, Herpesviridae
Murine leukemia virus, Retroviridae
Murine parainfluenza virus 1, Paramyxoviridae
Murine poliovirus, Picornaviridae
Murine polyomavirus, Papovaviridae
Murray Valley encephalitis virus, Flaviviridae
Nairobi sheep disease virus, Bunyaviridae
Ovine adeno-associated virus, Parvoviridae
Ovine adenoviruses 1 to 6, Adenoviridae
Ovine astrovirus 1, Astroviridae
Ovine herpesvirus 1, Herpesviridae
Ovine herpesvirus 2, Herpesviridae
Ovine pulmonary adenocarcinoma virus, Retroviridae
Patas monkey herpesvirus pH delta, Herpesviridae
Penguinpox virus, Poxviridae
Pneumonia virus of mice, Paramyxoviridae
Porcine adenoviruses 1 to 6, Adenoviridae
Porcine astrovirus 1, Astroviridae
Porcine circovirus, Circoviridae
Porcine enteric calicivirus, Caliciviridae
Porcine enterovirus 1 to 11, Picornaviridae
Porcine epidemic diarrhea virus, Coronaviridae
Porcine hemagglutinating encephalomyelitis virus, Coronaviridae
Porcine parvovirus, Parvoviridae
Porcine respiratory and reproductive syndrome, Arterivirus
Porcine rubulavirus, Paramyxoviridae
Porcine transmissible gastroenteritis virus, Coronaviridae
Porcine type C oncovirus, Retroviridae
Porpoise distemper virus, Paramyxoviridae
Primate calicivirus, Caliciviridae
Rabbit coronavirus, Coronaviridae
Rabbit fibroma virus, Poxviridae
Rabbit hemorrhagic disease virus, Caliciviridae
Rabbit kidney vacuolating virus, Papovaviridae
Rabbit oral papillomavirus, Papovaviridae
Rabbitpox virus, Poxviridae
Rabies virus, Rhabdoviridae
Raccoon parvovirus, Parvoviridae
Raccoonpox virus, Poxviridae
Red deer herpesvirus, Herpesviridae
Red kangaroopox virus, Poxviridae
Reindeer herpesvirus, Herpesviridae
Reindeer papillomavirus, Papovaviridae
Reovirus 1, Reoviridae
Reovirus 2, Reoviridae
Reovirus 3, Reoviridae
Reticuloendotheliosis virus, Retroviridae
Rhesus HHV-4-like virus, Herpesviridae
Rhesus leukocyte associated herpesvirus strain 1, Herpesviridae
Rhesus monkey cytomegalovirus, Herpesviridae
Rhesus monkey papillomavirus, Papovaviridae
Rubella virus, Togaviridae
Sealpox virus, Poxviridae
Sendai virus, Paramyxoviridae
Sheep associated malignant catarrhal fever of, Herpesviridae
Sheep papillomavirus, Papovaviridae
Sheep pulmonary adenomatosis associated herpesvirus, Herpesviridae
Sheeppox virus, Poxviridae
Simian adenoviruses 1 to 27, Adenoviridae
Simian agent virus 12, Papovaviridae
Simian enterovirus 1 to 18, Picornaviridae
Simian foamy virus, Retroviridae
Simian hemorrhagic fever virus, Arterivirus
Simian hepatitis A virus, Picornaviridae
Simian immunodeficiency virus, Retroviridae
Simian parainfluenza virus 10, Paramyxoviridae
Simian parainfluenza virus 41, Paramyxoviridae
Simian parainfluenza virus 5, Paramyxoviridae
Simian rotavirus SA11, Reoviridae
Simian sarcoma virus, Retroviridae
Simian T-lymphotropic virus, Retroviridae
Simian type D virus 1, Retroviridae
Simian vancella herpesvirus, Herpesviridae
Simian virus 40, Papovaviridae
Sindbis virus, Togaviridae
Skunkpox virus, Poxviridae
Spider monkey herpesvirus, Herpesviridae
Squirrel fibroma virus, Poxviridae
Squirrel monkey herpesvirus, Herpesviridae
Squirrel monkey retrovirus, Retroviridae
Swine cytomegalovirus, Herpesviridae
Swine infertility and respiratory syndrome virus, Arterivirus
Swinepox virus, Poxviridae
Tree shrew adenovirus 1, Adenoviridae
Tree shrew herpesvims, Herpesviridae
Vaccinia subspecies, Poxviridae
Vaccinia virus, Poxviridae
Varicella-zoster virus 1, Herpesviridae
Vesicular stomatitis Alagoas virus, Rkabdoviridae
Vesicular stomatitis Indiana virus, Rhabdoviridae
Vesicular stomatitis New Jersey virus, Rhabdoviridae
West Nile virus, Flaviviridae
Western equine encephalitis virus, Togaviridae
Woodchuck hepatitis B virus, Hepadnaviridae
Woodchuck herpesvirus marmota 1, Herpesviridae
Woolly monkey sarcoma virus, Retroviridae
Yaba monkey tumor virus, Poxviridae
Yellow fever virus, Flaviviridae In addition to viruses, other infectious agents may also be targeted according to the present invention, including bacteria, as well as molds, fungi and parasites. Bacterial infections agents include:

*Bacillus* spp.
*Bacteroides fragilis*
*Bordetella bronchiseptica*
*Bordetella parapertussis*
*Bordetella pertussis*
*Borrelia burgdorferi*
*Branhamella (Moraxella) catarrhalis*
*Branhamella (Moraxella) catarrhalis* (non β lactamase producer)
*Branhamella (Moraxella) catarrhalis* (β lactamase producer)
*Campylobacter jejuni*
*Campylobacter pylori*

*Corynebacterium* JK
*Enterococcus faecalis*
*Enterococcus faecium*
*Enterococcus* spp.
*Haemophilus ducreyi*
*Haemophilus influenzae*
*Haemophilus influenzae* (non β lactamase producer)
*Haemophilus influenzae* (β lactamase producer)
*Haemophilus influenzae* (penicillin susceptible)
*Haemophilus influenzae* (penicillin resistant)
*Haemophilus parainfluenzae*
*Legionella* spp.
*Legionella pneumophila*
*Listeria monocytogenes*
*Listeria monocytogenes*
*Mycoplasma hominis*
*Mycoplasma pneumoniae*
*Neisseria gonorrhoeae*
*Neisseria gonorrhoeae* (non beta lactamase producer)
*Neisseria gonorrhoeae* (beta lactamase producer)
*Neisseria meningitidis*
*Nocardia asteroides*
*Staphylococcus aureus*
*Staphylococcus aureus* (penicillin susceptible)
*Staphylococcus aureus* (penicillin resistant)
*Staphylococcus aureus* (methicillin susceptible)
*Staphylococcus aureus* (methicillin resistant)
*Staphylococcus coagulase* f
*Staphylococcus coagulase* f (non β lactamase producer)
*Staphylococcus coagulase* f (β lactamase producer)
*Staphylococcus epidermidis*
*Staphylococcus haemolyticus*
*Staphylococcus hominis*
*Streptococcus agalactiae*
*Streptococcus pneumoniae*
*Streptococcus pyogenes*
*Streptococcus* spp.
*Ureaplasma urealyticum*
*Mycoplasma hominis*
*Mycoplasma pneumoniae*
*Staphylococcus aureus*
*Ureaplasma urealyticum*

As noted above antibodies to autoantigens can be prepared using the methods described herein. An autoantigen is usually a normal protein or complex of proteins (and sometimes DNA or RNA) that is recognized by the immune system of a subject, for example a subject suffering from an autoimmune disease. These antigens are normally not the target of the immune system, but can become a target due to mainly genetic, environmental or other factors that cause the normal immunological tolerance for such an antigen to be lost. Autoantigens that can generate antibodies include, but are not limited to: acetylcholine receptor, adenine nucleotide translocator (ANT), aromatic L-amino acid decarboxylase, asialoglycoprotein receptor, bactericidal/permeability-increasing protein (Bpi), calcium-sensing receptor, cholesterol side-chain cleavage enzyme, collagen type IV, cytochrome P450 2D6 (CYP2D6), desmin, desmoglein 1, desmoglein 3, f-actin, GM gangliosides, glutamate decarboxylase (GAD65), glutamate receptor (GLUR), H/K ATPase, 17-beta-Hydroxylase (CYP17), 21-hydroxylase (CYP21), IA-2 (ICA512), insulin, insulin receptor, intrinsic factor type 1, leukocyte function-associated antigen (LFA-1), myelin-associated glycoprotein (MAG), myelin basic protein, myelin oligodendrocyte glycoprotein (MOG), myosin, p-80-coilin, pyruvate dehydrogenase complex-E2 (PDC-E2), sodium iodide symporter (NIS), SOX-10, thyroid and eye muscle shared protein, thyroglobulin, thyroid peroxidase, thyrotropin receptor, tissue transglutaminase, transcription coactivator p75, tryptophan hydroxylase, tyrosinase, tyrosine hydroxylase, ACTH, aminoacyl-tRNA histidyl synthetase, aminoacyl-tRNA synthetase (several), cardiolipin, carbonic anhydrase II, collagen (multiple types), centromere-associated proteins, DNA-dependent nucleosome-stimulated ATPase, fibrillarin, fibronectin, glucose-6-phosphate isomerase, □2-glycoprotein I (□2-GPI), golgin, heat shock protein, hemidesmosomal protein 180, histone H2A-H2B-DNA, IgE receptor, keratin, Ku-DNA-protein kinase, Ku-nucleoprotein, La phosphoprotein (La 55-B), myeloperoxidase, proteinase 3 (PR3), RNA polymerase I-III (RNP), signal recognition protein (SRP54), topoisomerase-I (Scl-70), tubulin, vimentin, C1 inhibitor, C1q, cytokines (IL-1α, IL-1β, IL-6, IL-10, LIF), factor II, factor V, factor VII, factor VIII, factor IX, factor X, factor XI, factor XII, thrombin, vWF, glycoprotein IIb/IIIg and Ib/IX, oxidized LDL, amphiphysin, cyclin B1, DNA topoisomerase II, desmoplakin, gephyrin, Hu proteins, neuronal nicotinic acetylcholine receptor, p53, p62 (IGF-II mRNA-binding protein), recoverin, Ri protein, synaptotagmin, voltage-gated calcium channels, yo protein.

Antibodies to tumor antigens can also be prepared. Tumor antigens are those antigens that are presented by MHC I or MHC II molecules on the surface of tumor cells. These antigens can sometimes be presented only by tumor cells and not by normal cells. In this case, they are called tumor-specific antigens (TSAs) and typically result from a tumor specific mutation. More common are antigens that are presented by tumor cells and normal cells, and they are called tumor-associated antigens (TAAs). Cytotoxic T lymphocytes that recognized these antigens may be able to destroy the tumor cells before they proliferate or metastasize. Tumor antigens can also be on the surface of the tumor in the form of, for example, a mutated receptor, in which case they will be recognized by B cells. Tumor antigens include the MAGE (1-10) and BAGE proteins, MUC-1, CEA, 17-1A, TRP-2, M-urinary antigen, M-fetal antigen, UTAA, GM2 ganglioside, GD2 ganglioside, hTRT, cytokeratin 19, SCCA-1 and -2, Orf73, PSA, CA 19-9, CA 72-4, CA 195, CA 55.1, NOVA2, CA 125, ART1, CASA, CO-029.

Use of Antibodies

Antibodies generated using the methods described herein can be used in any method that antibodies produced by other means cane be used. Thus, they can be used in passive therapy and diagnosis. The methods can be used to generate antibodies that are analyzed to characterize immune responses. Such characterization is important in various fields, including epidemiology, vaccine development and drug development.

Passive antibody immunization can provide a state of immediate immunity that can last for weeks and possibly months. Some human IgG isotypes have serum half-lives in excess of 30 days, which would confer long-lived protection to passively immunized persons. Where active vaccines are available, they may be administered together with antibodies to both immediate and long-lasting protection (e.g., for rabies in post-exposure prophylaxis). Administration of antibodies produced as described herein will follow the general protocols for passive immunization. Although passive antibodies are generally given systemically, oral administration can be useful against certain gastrointestinal agents. It may also be used possible to administer some antibody intramuscularly. Antibodies for administration be prepare in a formulation suitable for administration to a host. Aqueous compositions comprise an effective amount of an antibody dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Antibodies will generally be formulated for parenteral administration, e.g., formulated for injection via the intravenous, intramuscular, sub-cutaneous, intralesional, or even intraperitoneal routes. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

DESCRIPTION OF FIGURES

FIGS. 3A-3E: Analysis of the B-cell response induced by influenza vaccination. (A) ASCs were measured in blood by flow cytometry. Shown is the frequency of the ASC gate (CD32/CD202/low/CD191/CD27hi/CD38hi) for a representative donor and a summary for all ten donors normalized to total CD201/CD191 B-cell numbers. (B) Peripheral blood mononuclear cells (PBMCs) collected from ten donors were assayed for influenza-specific IgG secreting ASCs by ELISPOT assay at 0, 7, 14, 28 and 80 days after vaccination. Each sample was measured in duplicate, averaged and plotted as ASCs per million PBMCs over time post-vaccination. (C) HLA-DR and intracellular expression of Ki-67 by ASCs compared with naive or memory B cells. (D) Most ASCs at day 7 after influenza vaccination are influenza specific. Influenza- and total IgG-specific ELISPOT assays from several donors gave similar results. (E) Percentage of influenza-specific memory cells per total IgG-positive memory cells after mitogen stimulation as measured by ELISPOT at 0, 7, 14, 28 and 80 days post-vaccination as previously Described (Crotty et al. 2004 *J Immunol Methods* 286:111).

FIGS. 4A-4C: The ASC response after influenza vaccination is pauci-clonal and highly diversified by somatic hypermutation. (A) Comparison of the mean proportion (line) of all clonal variable region sequences from day-7 ASCs of 14 donors (points), including the bulkRNA of 104-105 ASCs fromten donors and verification by single-cell RT-PCR for four donors (average 37 sequences per donor). The ASCs were the most clonally related population (t-test, P#0.0003). Dotted lines indicate donors from which memory and ASCs were analysed simultaneously. Other B-cell populations were from historical data analysed in a similar fashion from our laboratory (see Methods and Figure descriptions). (B) Each point is the average frequency of somatic mutations per sequence from each donor (n values within Methods). On average, the anti-influenza ASCs had accumulated more mutations than either the IgG (t-test P50.003) or IgM (P5, 0.0001) memory and germinal-centre populations. GC, germinal centre. (C) The proportion of all variable genes from each B-cell population with the number of somatic mutations denoted in the legend (n values are at the centre of each pie chart).

FIG. 6A-6C: Specificity for the newly introduced influenza-B strain in the vaccine suggests a minimal impact of OAS. (A) Influenza-B strains used for the vaccine since 1989. Throughout the figure, strain names are color coded for the Yamagata lineage (green) and the Victoria lineage (orange/red). (B) Phylogenetic tree illustrating the similarity of recent influenza-B strains and the years in which each strain was included in the vaccine. The three vaccine strains tested (bold font) included B/Malaysia/2506/2004 (2006/7 season), which is most similar to the 2002-2004 strain (B/Hong Kong/33/2001). Conversely, the 2005/6 vaccine strain, B/Shanghai/361/2002, is more divergent. (C) All anti-B-strain antibodies reacted with equal or greater affinity to the current year's vaccines when tested by ELISA.

FIG. 7: Characteristics of anti-influenza antibodies.

FIGS. 10A-10D: Identification of individual antibody specificities. Each virus or vaccine specific antibody was tested by immunoprecipitation (I.P.) for extraction of particular influenza proteins from the reactive strain (or whole vaccine for those without particular strain reactivity). Those that did not precipitate any antigen by I.P. were tested for binding to the viral denatured proteins transferred to nitrocellulose membranes by Western blot. Examples of the various specificities detected are indicated for each viral strain (a-d) compared. As the antiinfluenza A (H3N2) antibodies each bound equally to either of the very similar A/California/7/2004 (2005/6 vaccine) and A/Wisconsin/67/2005 (2006/7 vaccine) strains, the latter strain to which most donors were vaccinated was used for IP. For five of the 53 reactive antibodies an antigen could not be determined. These antibodies were typically low affinity and somewhat polyreactive suggesting that the ASCs may have been non-specifically recruited to the immune response after accination. Some antibodies appeared to cross-react to both the A and B strains by ELISA (FIG. 9) and so all were tested by I.P. and Western blot for cross reactivity to the heterosubtypic influenza virus strains as well. Of the eight antibodies tested, two (D2-8 and D4-4) were found to I.P. HA from both the Influenza B and A strains. The findings of these experiments are summarized in FIG. 5C and in FIG. 7.

FIG. 11: Representative ASC antibodies can neutralize influenza infection of MDCK cells. All three anti-H3N2 antibodies tested neutralized A/Wisconsin/67/2005 infectivity (D1-8 and D1-9 from donor 1, and D3-4 from donor 3) an anti-B/Shanghai/361/2002 antibody tested from donor 6 could neutralize viral infectivity. Half-maximal tissue-culture infectious dosages of virus were neutralized in the percentage of replicate wells indicated (Y axis) at various dilutions of antibody (X axis). The negative control antibody is an anti-A/New Caledonia/20/99 (H1N1) antibody that as expected does not neutralize the H3N2 or B influenza strains.

DETAILED DESCRIPTION

In the first Example below, one embodiment of the method for generating human monoclonal antibodies is described. In the second Example below two different vaccine formulations (Fluvirin and Pneumovax23) were used to generate hmAbs. Fluvirin is primarily influenza HA and NA proteins, whereas the Pneumovax23 is produced from highly purified capsular polysaccharides from the 23 most prevalent or invasive pneumococcal types of Streptococcus pneumoniae (21). When purifying PBMCs from 30 ml of blood 7 d after vaccination, it should be possible to isolate several thousand IgG-positive ASCs. Because the single cell sorting process is highly efficient, typically 6-10 half plates can easily be sorted in this manner per donor. A half plate of cells (42 wells because Row H of the plate is left open for controls) yields about 20 antibodies. When the light chain of interest is kappa, typically, 70% of the antibodies will be kappa positive, the remaining being lambda and thus unamplified (29 antibodies). Of these, the heavy chain PCR efficiency is also close to 70% (20 antibodies). These RT-PCR efficiencies likely arise from a variety of factors, including stability of the RNA template from only a single cell, calibration of the flow cytometer to err on the side of having no cell rather than two cells within a well and limitations of the PCR that we have never overcome (such as occasional V genes that are not primed by the set of primers). Generally, several antibodies will not PCR correctly from the cloning PCR and a few others will be lost through the cloning process. As described in greater detail below, we found that for anti-influenza antibodies, approximately 40% of the ASCs were clonally related (from the same progenitor B cell) but with their antibody sequences differing by accumulated somatic hypermutations. Other vaccines or acute immunizations may have more or less clones. In our hands, even with variations in the frequency of mutations, two antibodies from the same clonal expansion are quite similar in binding characteristics. Thus, unless relevant to the experiment only one of a clone need be expressed. The end yield of transfectable antibodies containing a valid heavy and light chain will be 10-16 per half plate of cells sorted. Almost all will yield enough antibody (450 mg/ml) upon transfection for use in further assays. As an example, when using either Fluvirin or neumovax23, an average of 70% of the antibodies bound to the immunizing antigen(s) as measured by ELISA assays. For typical antibodies, transfecting four plates of 293A cells will yield a final concentration of 100-500 mg/ml of purified antibody. Variations in the immune systems of the donors utilized can cause variations in the yield of antibodies produced. Because of these variations, the ELISpot procedure is a valuable adjunct to the antibody production procedure. Certain donors will respond poorly to the vaccination, perhaps having only 10-30% antigen-specific ASCs, thus the yield of antigen-specific antibodies will also be low. When attempting to make antibodies to a new vaccine, the ELISpot results will accurately predict the final yield of antibodies.

Example 1

General Protocol

Described below is an embodiment of a general method for preparing human antibodies from a vaccinated subject Lymphoprep and B-Cell Enrichment 1) Collect blood 7 d post-vaccination into acid citric dextrose blood collection tubes (typically 1 for ELISpot, 4 for sort, 40-50 ml of blood total).
2) Add RosetteSep at 2.5 μl/ml to whole blood. Mix well. Best results occur if the lymphoprep is begun immediately after collection of the blood but may be done within 18 h of collection. If necessary store blood overnight, store as whole blood at 4° C. and perform lymphoprep immediately prior to staining and cell sorting. The ASCs can become unstable and die when removed from whole blood and stored overnight or when frozen.
3) Incubate at room temperature (20-25° C.) for 20 min.
4) Dilute the blood with an equal volume of PBS.
5) Add 15 ml of LSM to a separate 50-ml conical tube. Carefully layer diluted blood over the LSM. Layer no more than 30 ml of diluted blood over 15 ml of LSM. Use multiple tubes if necessary.

Figure 1:
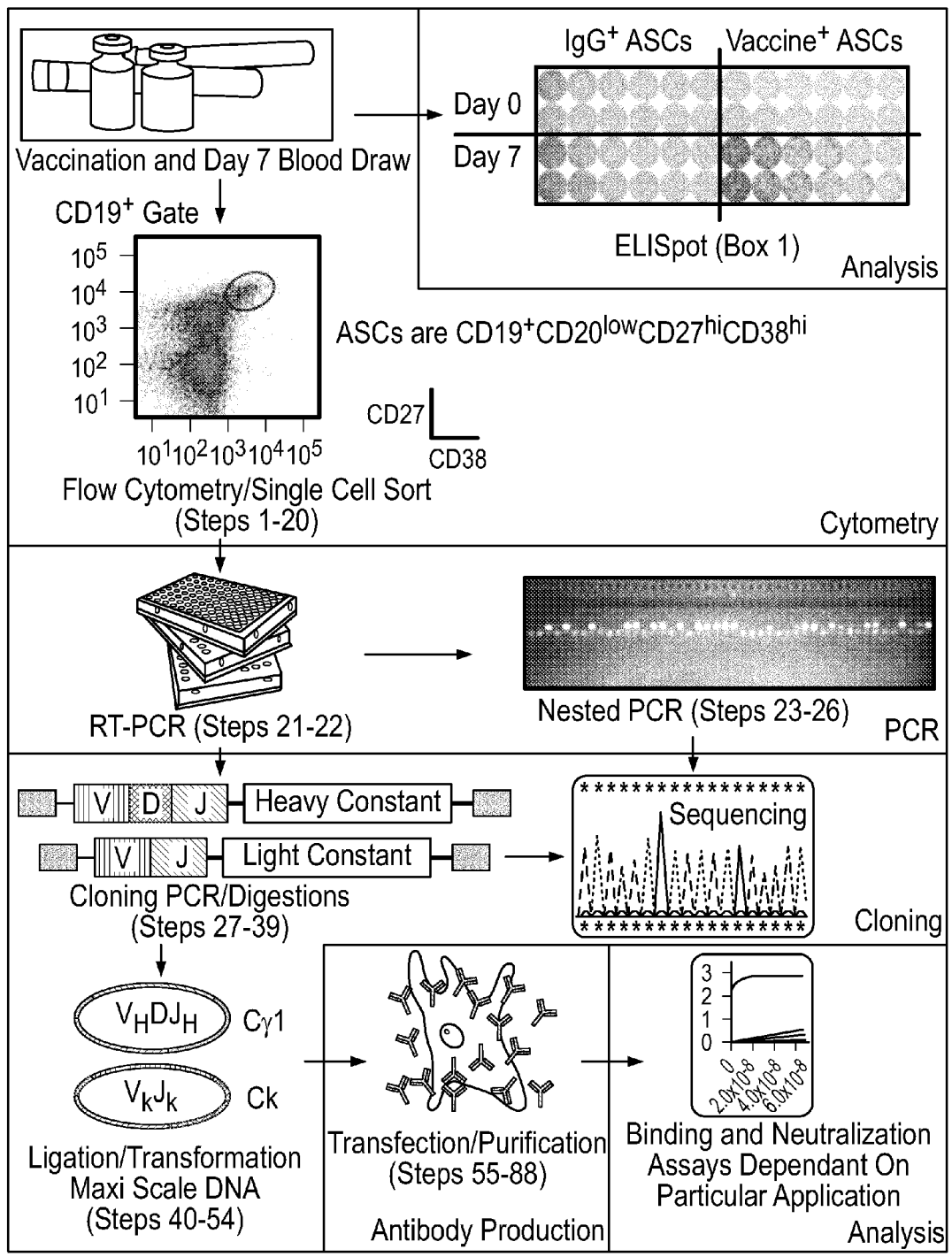
FIG. 1: Schematic depiction of an example of the method for preparing human antibodies.

6) Centrifuge for 30 min at 800 g at room temperature with no brake.
7) After centrifugation, the enriched PBMCs will form a band at the interface between the serum and the LSM. Remove this band with a Pasteur pipette and transfer to a new 50-ml centrifuge tube.
8) Rinse the enriched PBMCs by diluting to 50 ml with PBS, centrifuge for 5-10 min at 800 g at room temperature with no brake, then remove the supernatant.
9) If using more than one tube, combine the cells. Repeat Step 8, decreasing the centrifugation speed to 360 g. Brake may be used.

TABLE 1

Primer sequences

| Primer | Sequence | Use |
|---|---|---|
| 5' L-VH 1 | ACAGGTGCCCACTCCCAGGTGCAG (SEQ ID NO: 1) | RT-PCR |
| 5' L-VH 3 | AAGGTGTCCAGTGTGARGTGCAG (SEQ ID NO: 2) | RT-PCR |
| 5' L-VH 4/6 | CCCAGATGGGTCCTGTCCCAGGTGCAG (SEQ ID NO: 3) | RT-PCR |
| 5' L-VH 5 | CAAGGAGTCTGTTCCGAGGTGCAG (SEQ ID NO: 4) | RT-PCR |
| 5' AgeI VH1/5/7 | CTGCAACCGGTGTACATTCCGAGGTGCAGCTGGTGCAG (SEQ ID NO: 5) | Cloning PCR |
| 5' AgeI VH3 | CTGCAACCGGTGTACATTCTGAGGTGCAGCTGGTGGAG (SEQ ID NO: 6) | Cloning PCR |
| 5' AgeI VH3-23 | CTGCAACCGGTGTACATTCTGAGGTGCAGCTGTTGGAG (SEQ ID NO: 7) | Cloning PCR |
| 5' AgeI VH4 | CTGCAACCGGTGTACATTCCCAGGTGCAGCTGCAGGAG (SEQ ID NO: 8) | Cloning PCR |
| 5' AgeI VH 4-34 | CTGCAACCGGTGTACATTCCCAGGTGCAGCTACAGCAGTG (SEQ ID NO: 9) | Cloning PCR |
| 5' AgeI VH 1-18 | CTGCAACCGGTGTACATTCCCAGGTTCAGCTGGTGCAG (SEQ ID NO: 10) | Cloning PCR |
| 5' AgeI VH 1-24 | CTGCAACCGGTGTACATTCCCAGGTCCAGCTGGTACAG (SEQ ID NO: 11) | Cloning PCR |
| 5' AgeI VH 3-9/30/33 | CTGCAACCGGTGTACATTCTGAAGTGCAGCTGGTGGAG (SEQ ID NO: 12) | Cloning PCR |
| 5' AgeI VH 6-1 | CTGCAACCGGTGTACATTCCCAGGTACAGCTGCAGCAG (SEQ ID NO: 13) | Cloning PCR |
| 5' L Vκ 1/2 | ATGAGGSTCCCYGCTCAGCTGCTGG (SEQ ID NO: 14) | RT-PCR |
| 5' L Vκ 3 | CTCTTCCTCCTGCTACTCTGGCTCCCAG (SEQ ID NO: 15) | RT-PCR |
| 5' L Vκ 4 | ATTTCTCTGTTGCTCTGGATCTCTG (SEQ ID NO: 16) | RT-PCR |
| 5' Pan Vκ | ATGACCCAGWCTCCABYCWCCCTG (SEQ ID NO: 17) | Nested PCR/sequen |
| 5' AgeI Vκ 1 | CTGCAACCGGTGTACATTCTGACATCCAGATGACCCAGTC (SEQ ID NO: 18) | Cloning PCR |
| 5' AgeI Vκ 1-9/1-13 | TTGTGCTGCAACCGGTGTACATTCAGACATCCAGTTGACCCAGTCT (SEQ ID NO: 19) | Cloning PCR |
| 5' AgeI Vκ 10-43/1-8 | CTGCAACCGGTGTACATTGTGCCATCCGGATGACCCAGTC (SEQ ID NO: 20) | Cloning PCR |
| 5' AgeI Vκ 2 | CTGCAACCGGTGTACATGGGGATATTGTGATGACCCAGAC (SEQ ID NO: 21) | Cloning PCR |
| 5' AgeI Vκ 2-28/2-30 | CTGCAACCGGTGTACATGGGGATATTGTGATGACTCAGTC (SEQ ID NO: 22) | Cloning PCR |
| 5' Age Vκ 3-11/30-11 | TTGTGCTGCAACCGGTGTACATTCAGAAATTGTGTTGACACAGTC (SEQ ID NO: 23) | Cloning PCR |

TABLE 1-continued

Primer sequences

| Primer | Sequence | Use |
|---|---|---|
| 5' Age Vκ 3-15/30-15 | CTGCAACCGGTGTACATTCAGAAATAGTGATGACGCAGTC (SEQ ID NO: 24) | Cloning PCR |
| 5' Age Vκ 3-20/30-20 | TTGTGCTGCAACCGGTGTACATTCAGAAATTGTGTTGACGCAGTCT (SEQ ID NO: 25) | Cloning PCR |
| 5' Age Vκ 4-1 | CTGCAACCGGTGTACATTCGGACATCGTGATGACCCAGTC (SEQ ID NO: 26) | Cloning PCR |
| 5' L Vλ 1 | GGTCCTGGGCCCAGTCTGTGCTG (SEQ ID NO: 27) | RT-PCR |
| 5' L Vλ 2 | GGTCCTGGGCCCAGTCTGCCCTG (SEQ ID NO: 28) | RT-PCR |
| 5' L Vλ 3 | GCTCTGTGACCTCCTATGAGCTG (SEQ ID NO: 29) | RT-PCR |
| 5' L Vλ 4/5 | GGTCTCTCTCSCAGCYTGTGCTG (SEQ ID NO: 30) | RT-PCR |
| 5' L Vλ 6 | GTTCTTGGGCCAATTTTATGCTG (SEQ ID NO: 31) | RT-PCR |
| 5' L Vλ 7 | GGTCCAATTCYCAGGCTGTGGTG (SEQ ID NO: 32) | RT-PCR |
| 5' L Vλ 8 | GAGTGGATTCTCAGACTGTGGTG (SEQ ID NO: 33) | RT-PCR |
| 5' AgeI Vλ 1 | CTGCTACCGGTTCCTGGGCCCAGTCTGTGCTGACKCAG (SEQ ID NO: 34) | Cloning PCR |
| 5' AgeI Vλ 2 | CTGCTACCGGTTCCTGGGCCCAGTCTGCCCTGACTCAG (SEQ ID NO: 35) | Cloning PCR |
| 5' AgeI Vλ 3 | CTGCTACCGGTTCTGTGACCTCCTATGAGCTGACWCAG (SEQ ID NO: 36) | Cloning PCR |
| 5' AgeI Vλ 4/5 | CTGCTACCGGTTCTCTCTCSCAGCYTGTGCTGACTCA (SEQ ID NO: 37) | Cloning PCR |
| AgeI Vλ 6 | CTGCTACCGGTTCTTGGGCCAATTTTATGCTGACTCAG (SEQ ID NO: 38) | Cloning PCR |
| 5' AgeI Vλ 7/8 | CTGCTACCGGTTCCAATTCYCAGRCTGTGGTGACYCAG (SEQ ID NO: 39) | Cloning PCR |
| Ab-vec-sense | GCTTCGTTAGAACGCGGCTAC (SEQ ID NO: 40) | Sequencing |
| VH3a-sense | SARGTGCAGCTCGTGGAG (SEQ ID NO: 41) | Nested PCR/sequen |
| VH3b-sense | GAGGTGCAGCTGTTGGAG (SEQ ID NO: 42) | Nested PCR/sequen |
| HuIgG-const-anti | TCTTGTCCACCTTGGTGTTGCT (SEQ ID NO: 43) | RT-PCR |
| 3' Cμ CH1 | GGGAATTCTCACAGGAGACGA (SEQ ID NO: 44) | RT-PCR |
| MuD | GGAATTCTCACAGGAGACGA (SEQ ID NO: 45) | Nested PCR |
| PW-Cgamma | AGTAGTCCTTGACCAGGCAGCCCAG (SEQ ID NO: 46) | Nested PCR |
| 3' SolI JH 1/2/4/5 | TGCGAAGTCGACGCTGAGGAGACGGTGACCAG (SEQ ID NO: 47) | Cloning PCR |
| 3' SolI JH 3 | TGCGAAGTCGACGCTGAAGAGACGGTGACCATTG (SEQ ID NO: 48) | Cloning PCR |

TABLE 1-continued

Primer sequences

| Primer | Sequence | Use |
|---|---|---|
| 3' SolI JH 6 | TGCGAAGTCGACGCTGAGGAGACGGTGACCGTG (SEQ ID NO: 49) | Cloning PCR |
| 3' Cκ 543-566 | GTTTCTCGTAGTCTGCTTTGCTCA (SEQ ID NO: 50) | RT-PCR |
| 3' Cκ 494-516 | GTGCTGTCCTTGCTGTCCTGCT (SEQ ID NO: 51) | Nested PCR |
| 3' BsiWI Jκ 1/2/4 | GCCACCGTACGTTTGATYTCCACCTTGGTC (SEQ ID NO: 52) | Cloning PCR |
| 3' BsiWI Jκ 3 | GCCACCGTACGTTTGATATCCACTTTGGTC (SEQ ID NO: 53) | Cloning PCR |
| 3' BsiWI Jκ 5 | GCCACCGTACGTTTAATCTCCAGTCGTGTC (SEQ ID NO: 54) | Cloning PCR |

Staining and Flow Cytometry

Figure 2:
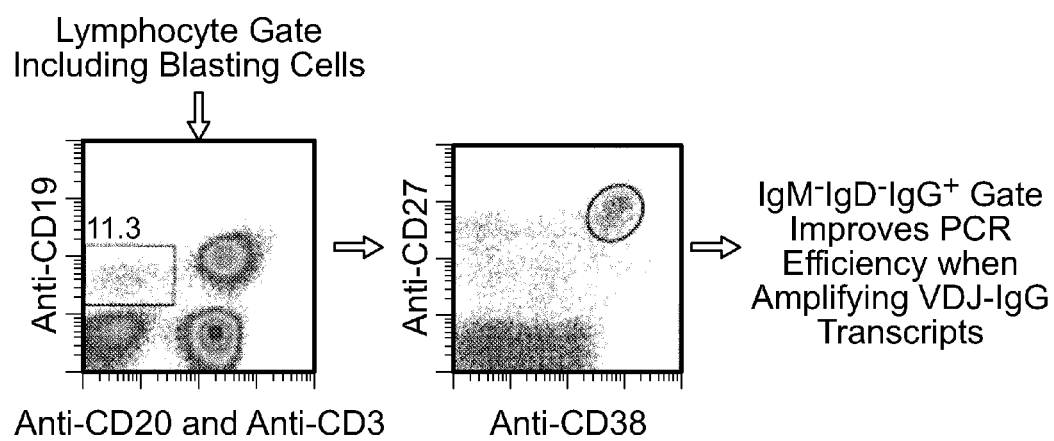
FIG. 2: Representative flow data summarizing an example of the cell isolation strategy. First, the live cell gate is set, including blasting cells, then $CD19^{high}/CD201^{ow}$ to $^{neg}/CD3^{neg}$ and $CD27^{high}/CD38^{high}$. Finally, appropriate IgG, IgM, and IgD gates are set to obtain the precise population of interest, improving the immunoglobulin constant region-specific priming efficiency.

10) To ensure that enough ASCs are obtained from the sorting process, begin with 4-8 million of enriched PBMCs prepared in Steps 1-9.
11) If the cells appear bloody (i.e., contain significant amounts of red blood cells), clear with ACK buffer (add 1 ml of ACK for 1-2 min). Wash the cells twice with PBS. Filter the cells through a 40-mm cell strainer to remove clumps.
12) Resuspend approximately 3 million cells in 100 μl of staining buffer; these are the cells that will be used for sorting. In addition, prepare one aliquot of cells (about $0.5 \times 10^6$ cells in 100 μl of staining buffer) for each fluorophore to be tested in Step 13 and one aliquot of cells that will remain unstained. These compensation controls will be used to adjust the sensitivity of the flow cytometer detectors to avoid overlap of the emission spectra when the various flourophores are combined. All buffers for staining should contain 2% FCS (vol/vol) in PBS to block nonspecific staining.
13) Add the following antibodies to the aliquot of cells for sorting: CD3 FITC; anti-CD27 PE; anti-CD38 APC-Cy5.5; anti-CD20 FITC; anti-CD19 PE-Alexa Fluor 610; mouse anti-human IgM-biotin; anti-IgG-Alexa 647 and anti-IgD-Alexa 405. In addition, add one of the fluorophore-conjugated antibodies to each of the compensation control aliquots of cells prepared in Step 12. The specific amounts of each antibody used should be titrated to give distinct single color populations before setting up a new experiment. Appropriate species-specific isotype control antibodies should be used to distinguish specifically stained populations from any background staining that might occur.
14) Incubate the cells for 30 min at 4° C.
15) Wash twice with 200 μl of 2% FCS in PBS.
16) Add 1:500 Streptavidin PE-Cy7 and incubate for 20 min at 4° C.
17) Wash twice again; pass the cells through another cell strainer to avoid clogs in the cytometer.
18) Gate the cells as shown in the strategy in FIG. 2. Alternatively, the gating scheme illustrated in FIG. 1 has also been used without affecting the isolation of specific ASCs. ASCs are then further enriched based on IgG or any other isotype desired.
19) Bulk sort the cells into tubes containing 2% FCS in PBS buffer collecting the cells gated as above.
20) Re-sort the cells on forward versus side scatter (live cell gate with doublet discrimination) into single cell PCR plates containing 10 μl of RNase-inhibiting RT-PCR catch buffer. To facilitate the RT-PCR step, sort only into half of the plate and do not put cells in Row H (catch buffer should be added to this row to allow for PCR negative controls). Immediately seal each plate with a microseal foil label and place on dry ice until the cell sorting is finished when plates can be placed in a −80° C. freezer. Use RNase-free precautions for Step 20. As the catch buffer is hypotonic, the cells are lysed, and with immediate freezing, their RNA is protected by the included RNase inhibitor. It is necessary to use multiple buffer controls (row H) because the likelihood of PCR contamination increases substantially with the many cycles of PCR required to amplify the variable genes from single B cells. At this point the plates may be stored for months to several years if they are immediately flash frozen on dry ice after the collection and kept at −80° C.

Reverse Transcription, Nested and Cloning PCRs

21) Thaw a plate of single cells on ice and prepare the RT-PCR master mix following the Qiagen OneStep RT-PCR Kit protocol. Do not use the 'Q' solution. The primers for the master mix have been previously published (Wardemann et al. 2003 Science 301, 1374-1377; Tiller et al. 2008 J. Immunol. Methods 329, 112-124) and are used from 0.6 mM stocks (see Table 1). A total of nine primers are included to amplify all of the heavy and light chain family genes. The RT-PCR enzyme mix and completed master mix should be kept on ice at all times. (RT-PCR primers for IgG heavy chain and kappa light chain are: HuIgG-const-anti, 3' Cκ 543-566, 5' L Vκ 4, 5' L Vκ 3, 5' L Vκ 1/2, 5' L-VH 5, 5' L-VH 4/6, 5' L-VH 3 and 5' L-VH 1). Alternatively, Igλ amplification can be performed by replacing the Igκ primers with: 3' Cλ and 5' L Vλ1, L Vλ2, L Vλ 3, L Vλ14/5, L Vλ16, L Vλ7 and L Vλ8 primers. RNase-free precautions should be used for this step and the next step.
22) Carefully add 15 μl of the master mix to each well of the plate and then carefully apply dome lids to the plate. Use the program suggested in the OneStep protocol. Program: 50 lC for 30 min for the RT, 95° C. for 15 min ('Hot start' to deactivate RT and activate thermal Taq), 40 cycles of 95° C. for 1 min, 55° C. for 1 min and 72° C. for 1 min. Great care must be used during this step since even talking over the plate can cause contamination. It is also important to carefully remove the dome caps after the reaction to avoid splashes.

23) Prepare the nested PCR master mixes: 24 µl for each well (1.2 ml for half a plate) as described in the table below. One master mix is necessary for the light chain and one mix is necessary for the VH3 family heavy chain. The VH3 primer will amplify VH genes from most other families as well. For completeness, a separate VH1/5 and VH4 nested PCR may be done as well (see Table 1 for primers), though these reactions identify the variable genes of most cells if performed separately.

| Reagent for PCR | Volume (µl) for each (25 µl sample) | Final concentration (with template) |
|---|---|---|
| Taq DNA Polymerase (added last) | 0.25 | 50 U ml$^{-1}$ |
| 10x buffer | 2.5 | 1x |
| dNTPs (10 mM each, combined) | 0.5 | 200 µM |
| Forward primer: VH3a and VH3b or PanVκ | 0.5 | 1.2 µM |
| Reverse primer: PW-Cgamma or CK494-516 | 0.5 | 1.2 µM |
| dH$_2$O (nuclease free) | 17.25-19.25 (to 24 µl total volume) | — |
| Template | 1.0 | — |

24) Add the nested master mixes to a new single cell PCR plate (24 µl into each well). One half of the plate can be used for the heavy chain master mix and the other half for the light chain master mix (excluding row H). Carefully remove 1 µl of the RT product from one well of the single cell plate and add to both the corresponding heavy and light chain wells containing the master mix. Repeat for all 48 wells of the original RT plate (including the buffer controls in row H). Affix dome caps and run the PCR using the following conditions: 95° C. for 4 min, 40 cycles of 95° C. for 1 min, 57° C. for 1 min and 72° C. for 1.5 min.

25) Centrifuge the nested plates briefly and run 2 µl of each well on a 1% agarose gel (wt/vol). Positive results are determined by the visualization of a band at approximately 400 bp. Purify positive products with the QIAquick PCR Microcentrifuge Protocol, eluting with 40 µl of EB buffer.

26) Sequence each purified well using a mixture of the VH3a and VH3b primers (or the VH1/5 or VI-14 primers as appropriate) for the heavy products or PanVk or cloning-PCR VI primers for the kappa or lambda products, respectively. Use of the variable gene-specific (5') primers for sequencing helps to ensure identification of the J portion of the heavy chain VDJ or light chain VJ genes that is important for the cloning PCR in Step 27. Variable and junctional (J) gene segments can be identified using the immunoglobulin BLAST search engine at the NCBI website (http://www.ncbi.nlm.nih.gov/igblast/).

27) Prepare the cloning PCR master mixes as detailed in the table below. To ensure that the master mix is not contaminated, prepare each master mix with enough volume to have one buffer control (see Table 1 'Cloning PCR' primers). Many of the primers for the cloning PCR are used for several gene families as they prime conserved sequences. The targeted gene segments are all indicated in the name of the primer in Table 1. For example, the 5' AgeI VH1/5/7 primer is used for any gene from the VH1, VH5 or VH7 families; the 5' AgeI VH3-9/30/33 primer is used for either VH3-9, VH3-30 or VH3-33 genes; the 3' BsiWI Jk 1/2/4 primer is used for either Jk 1, Jk 2 or Jk 4.

| Reagent for PCR | Volume (µl) for each (25 µl total) | Final concentration (with template) |
|---|---|---|
| Taq DNA polymerase (added last) | 0.25 | 50 U ml$^{-1}$ |
| 10x buffer | 2.5 | 1x |
| dNTPs (10 mM each, combined) | 0.5 | 200 µM |
| 5' AgeI-VH or VK primer | 0.5 | 1.2 µM |
| 3' SalI-JH or 3' BsiWI-JK primer | 0.5 | 1.2 µM |
| dH$_2$O (nuclease free) | 19.75 | — |
| Template | 1.0 | — |

28) Add 1 µl of the RT product to each 24 µl of cloning PCR mix and apply dome caps as in Step 22. Products should be checked on a gel to ensure that a band is present and that the controls are not contaminated as described in Step 25. Run the PCR using the following conditions: 95° C. for 4 min, 35 cycles of 95° C. for 1 min, 57° C. for 1 min and 72 lC for 1.5 min.

PCR Purification

29) Follow the protocol outlined in the QIAquick PCR Microcentrifuge Protocol with one exception: to elute the DNA, apply 31 µl of PCR water to the column, let the column sit for 1 min and then centrifuge. For all centrifuging steps, centrifuge for 60 s at B17,900 g at room temperature as per Qiagen protocol. PCR products may be stored for up to 1 month at 20° C. First digestion of gamma, kappa or lambda chain variable gene inserts.

30) For all inserts: add 3.5 µl of NEB buffer 1 and 1 µl of AgeI to purified PCR products.

31) Mix the sample by pipetting up and down.

32) Overlay the sample with 40 µl of sterile mineral oil.

33) Incubate the samples for 4 h or overnight in a 37° C. water bath or heat block.

Digestion Purification

34) Purify using the same protocol as the 'PCR purification' in Step 29.

Second Digestion

35) For a gamma chain insert, add 3.5 µl NEB buffer 3, 0.35 µl BSA and 1 µl SalI to the purification product. For a kappa chain insert, add 3.5 µl NEB buffer 3 and 1 µl BsiWI to the purification product. For a lambda chain insert, add 3.5 µl NEB buffer 2, 0.35 µl BSA and 1 µl XhoI to the purification product.

36) Overlay the sample with 40 µl of sterile mineral oil.

37) Incubate the sample for 4 h or overnight in a water bath. For kappa inserts, incubate at 55° C. For gamma and lambda inserts, incubate at 37° C.

Gel Purification

38) Run all samples on a 1% agarose gel (wt/vol). The insert band will be approximately 400 bp in length.
39) Follow the protocol outlined in the QIAquick Gel Extraction Kit (using a microcentrifuge) with one exception: to elute the DNA, apply 34 µl of EB buffer to the column, let the column sit for 1 min and centrifuge. Note: all centrifuge steps are carried out for 60 s. After excising the insert band from the gel, you may store it at 4 lC overnight before proceeding with the remaining gel purification protocol. The final product may be stored for up to 1 year at −20° C.

Ligation

40) Vector and insert DNA concentrations should be calculated from the A260 reading of a spectrophotometer (an A260 of 1.0 is 50 mg/ml of pure double stranded DNA). A five-fold molar excess of insert to vector should be used. As the vector is approximately 5,700 bp and the insert is typically 350-400 by (variance is due to the CDR3 junction), a 3:1 ratio of vector to insert can be used.
41) Add 1 µl of vector (from a 1 µg/ml stock), 1 µl of T4 DNA ligase buffer, 1 µl of T4 ligase and an appropriate volume of the insert purification product to equal 0.3 mg into a clean 0.5-mi tube.
42) Add PCR water to a final volume of 10 ml. Incubate the sample overnight at 16° C. in a PCR machine or for 2 h at room temperature.

Transformation of DH5a Cells

43) Follow the protocol included with the DH5 a cells with the following exceptions: use 25 µl of DH5a cells and 3 µl of DNA, and plate the cells on an LB plate containing 50 µg/ml of ampicillin. Incubate the cultures for 2-3 h in SOC media at 37° C., and plate 100 µl of the transformation culture. Incubate the plates overnight at 37° C.
44) Choose four colonies from the plate to ensure a consensus variable gene sequence is identified. For each colony, inoculate one 14-ml round-bottom tube containing 5 ml of LB broth and ampicillin (50 µg/ml).
45) Incubate the tubes overnight, shaking at 225 r.p.m. on an orbital shaker, at 37° C.
46) Make glycerol stocks of each culture by transferring 300 ml of 1:1 sterile LB/glycerol and 700 ml of the confluent culture to a 2-ml tube, mix well and freeze at −80° C. These glycerol stocks are still viable after several years at −80° C.

Miniprep

47) Pellet bacteria by centrifuging the culture tubes (prepared in Steps 44 and 45) for 10 min at 800 g. Discard the supernatant.
48) Follow the protocol outlined in the QIAprep Spin Miniprep Kit Handbook (using a microcentrifuge) with one exception: elute the DNA with 40 µl of EB buffer. Note: all centrifuge steps are carried out for 60 s.
49) Sequence the eluted DNA with the AbVec primer (see Table 1).

Maxiprep

50) Compare the four mini-prep sequences using DNA sequence alignment software (Such as ClustalW: http://www.ebi.ac.uk/Tools/clustalw2/index.html). It is expected that some sequences will have accumulated base exchanges due to PCR errors but one of the four samples typically represents the consensus.
51) With a scraping from the glycerol stock of the colony of choice, inoculate one 14-ml round-bottom tube containing 5 ml of LB broth with ampicillin (50 µg/ml).
52) Incubate the tubes for 4-5 h, shaking at 225 r.p.m. on an orbital shaker, at 37° C.
53) Transfer the cultures to 500-ml flasks containing 250 ml of LB broth and ampicillin (50 µg/ml). Incubate the flasks overnight, shaking at 225 r.p.m. on an orbital shaker, at 37° C.
54) Follow the protocol outlined in the Genopure Plasmid Maxi Kit with the following exception: re-dissolve the plasmid DNA pellet in 400 µl of pre-warmed (50° C.) elution buffer.

Transfection of 293A Cells 55) 293A cells should be grown and passaged as per the product sheet from Invitrogen. Ensure that 293A cells are 80-90% confluent and evenly spread out across the 150 mm×25 mm tissue culture plate. It is important that the passage number for the 293A cells be kept below 30 passages; otherwise, the cells may not efficiently produce the antibody.
56) Warm DMEM media to room temperature; thaw PEI solution, heavy chain and light chain DNA.
57) For each plate to be transfected, aliquot 2.4 ml of DMEM into a conical vial. Add 9 µg of heavy chain DNA and 9 µg of light chain DNA per plate to the DMEM.
58) Add 100 ml of PEI solution per plate to the prepared DMEM and DNA mixture. Immediately vortex. Incubate at room temperature for 15 min.
59) Remove all but 18 ml of the culture media from each plate to be transfected.
60) Gently add 2.5 ml of PEI mixture to each plate, rocking the plate to ensure even distribution.
61) Incubate the cells with the PEI mixture in an incubator at 37° C. with 5% $CO_2$ for 24 h.
62) Change the culture media to basal media (20-25 ml per plate).
63) Collect the media from the plates 4 d later. The supernatant may be stored at 4° C. for several months if $NaN_3$ is added at a concentration of 0.05% (wt/vol). For some applications (i.e., ELISA), the antibody-containing supernatant is sufficient for testing the mAbs and the protein purification steps (Steps 64-77) can be optional. However, for long-term storage and more flexibility the antibodies are preferably purified.

Protein Purification

64) Prepare protein A agarose beads by adding approximately 1.5 ml of suspended beads to 50 ml of PBS in a 50-ml conical tube.
65) Centrifuge the tubes of beads for 10 min at 2,100 g at room temperature with no brake. Remove the PBS with an aspirator. Do not use brake on any of the centrifugations involving the agarose beads, as braking can damage the beads. Even slight breaking at the end of the spin can cause the beads to fluff, making it difficult to cleanly remove the supernatant.
66 Rinse each tube of beads with PBS (fill each tube with 50 ml of PBS and repeat Step 65).
67) Centrifuge the media collected from the transfection for 10 min at 900 g at room temperature, and then transfer the media from two plates (25 ml from each plate) to each tube of beads.
68) Incubate the media with the beads for 1-2 h at room temperature or overnight at 4° C. with slow agitation using a variable speed angle rocker. It works well to stabilize the tubes in a horizontal position.

69) Centrifuge the tubes of beads for 10 min at 2,100 g at room temperature with no brake. Remove the media with an aspirator.
70) Add 35 ml of 1 M NaCl to each tube. Centrifuge the tubes of beads for 10 min at 2,100 g at room temperature with no brake. Remove the 1 M NaCl with an aspirator.
71) Rinse each tube of beads with PBS (fill each tube with 35 ml of PBS and repeat Step 65).
72) Repeat Step 65.
73) Add 3-5 ml of 0.1 M glycine-HCl to each tube. Incubate on a tabletop shaker for 15 min.
74) Centrifuge the tubes of beads for 10 min at 2,100 g at room temperature with no brake. Transfer the glycine-HCl to a new vial. The time the antibodies are at low pH should be minimized as much as possible.
75) Adjust the pH to 7-7.4 with 1 M Tris-HCl. If there are beads in the vial, centrifuge the tubes for 10 min at 2,100 g at room temperature with no brake.
76) Transfer the neutralized sample to the top of an amicon protein concentrator; add PBS to a final volume of 15 ml. Centrifuge the concentrator for 8-12 min at 2,100 g at room temperature with brake on, until a volume of 0.5-1 ml is reached.
77) Transfer the concentrated antibody sample from the concentrator into a clean 1.5-ml tube. If desired, preserve the antibody by adding $NaN_3$ to 0.05% (wt/vol). Note that biological assays using live cells (i.e., viral infection neutralization assays) are sensitive to $NaN_3$.
78) To reuse the beads (up to 10 times as suggested by the manufacturer), add 15 ml of 0.1 M glycine-HCl to each tube of beads after 3-5 ml containing the antibody fraction is removed. Incubate on a tabletop shaker for 30 min, centrifuge for 10 min at 2,100 g at room temperature with no brake, remove the glycine-HCl with an aspirator, then rinse twice with PBS (according to Step 89). Store in conical vials with 50 ml of PBS containing 0.05% $NaN_3$ at 4° C. for up to 6 months.

Protein Quantification

79) Follow the protocol included with the EZQ Protein Quantification Kit with the following exception: stain the paper for 60 min. Protein concentrations can be checked using an alternative quantification method, such as anti-IgG ELISA assays relative to a good IgG standard, the Qubit Protein Quantification Kit or a spectrophotometer. For critical applications, verify the concentrations by more than one method.

Gel Confirmation of Protein Quality

80) Run the resulting purified antibodies on an SDS-PAGE gel (12% gel (vol/vol), 4% stacking (vol/vol), reducing conditions). The resulting bands for heavy chain will be between 50 and 60 kDa and the light chain will be between 20 and 25 kDa.

Reagents for Steps 1-80

Iggamma, Igkappa and Iglambda expression vectors: The expression vectors contain a murine immunoglobulin signal peptide sequence and variable-gene cloning sites upstream of the appropriate human immunoglobulin constant regions followed by an SV40 polyadenylation sequence. Transcription is under the HCMV (human cytomegalovirus immediate-early) promoter and clones are selected based on ampicillin resistance. The antibody variable-heavy and variable-light rearranged genes from each single cell are cloned into the respective vectors in frame with the signal peptide and constant region genes. These vectors are then co-transfected into the 293A cell line for expression. The resultant antibodies are properly trafficked and secreted after cleavage of the signal peptide, resulting in fully human IgG/kappa or IgG/lambda amino-acid sequences. The vector sequences are available through the NCBI GenBank (accession numbers: FJ475055, FJ475056 and FJ517647.

Basal media An aliquot of 250 ml each of sterile RPMI and DMEM; 3.75 ml of antibiotic/antimycotic and 5 ml each of L-glutamine (200 mM), 100× Nutridoma and sodium pyruvate (100 mM) was used. Basal media must be made fresh every 7 d. L-Glutamine can be stored at −20° C. for up to 1 year, Nutridoma can be stored at room temperature (20-25° C.) for up to 1 year and sodium pyruvate can be stored for up to 6 months at 4° C.

0.1 M glycine-HCl: Here 0.1 M glycine solution equilibrated to pH 2.7 with 12 M HCl and filter sterilized. Solution can be stored up to 60 d at room temperature.

1M Tris-HCl: Here 1M Tris solution equilibrated to pH 9.0 with HCl and filter sterilized. Solution can be stored up to 60 d at 4° C.

ACK lysing buffer: Here 0.15 M NH4Cl, 10 mM $KHCO_3$ and 0.1 mM $Na_2EDTA$. Adjust pH to 7.2-7.4 with 1 MHCl and filter sterilized. Solution can be stored up to 1 year at room temperature (20-25° C.).

LB agar plates: Dissolve LB agar in dH2O according to package directions and autoclaved. When cooled to 45° C., add 50 μg/ml ampicillin. Dispense 20-25 ml agar solution into 100 mm×15 mm petri dishes. Cool and store at 4° C. for up to 6 months.

AEC substrate Prepare AEC stock (20 mg/ml AEC in dimethylformamide). Dilute AEC from stock to 0.3 mg/ml in 0.1 M sodium acetate buffer (pH 5.0) just prior to use. Filter sterilized with a 0.45-mm syringe filter. The stock solution may be made and stored for up to 2 months. The diluted solution must be made fresh each time used.

RNAse-inhibiting RT-PCR catch buffer: To 5 ml of RNAse-free water, add 50 μl of 1 M Tris pH 8.0 and 125 μl of Rnasin. Keep on ice. This makes enough for 10 half plates. Catch buffer must be made fresh each time used.

PEI solution: It was prepared by 1 mg/ml PEI in 80° C. dH2O. Adjust pH to 7.2 with HCl. Filter sterilize with a 0.45-mm syringe filter. Store at −20° C. for up to 1 year.

Example 2

Figure 3C:
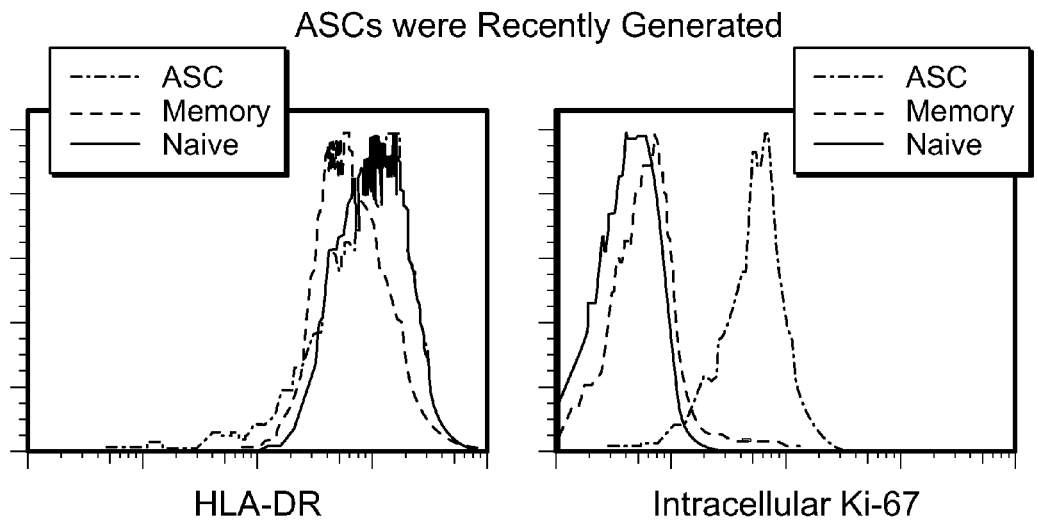
Figure 3D:
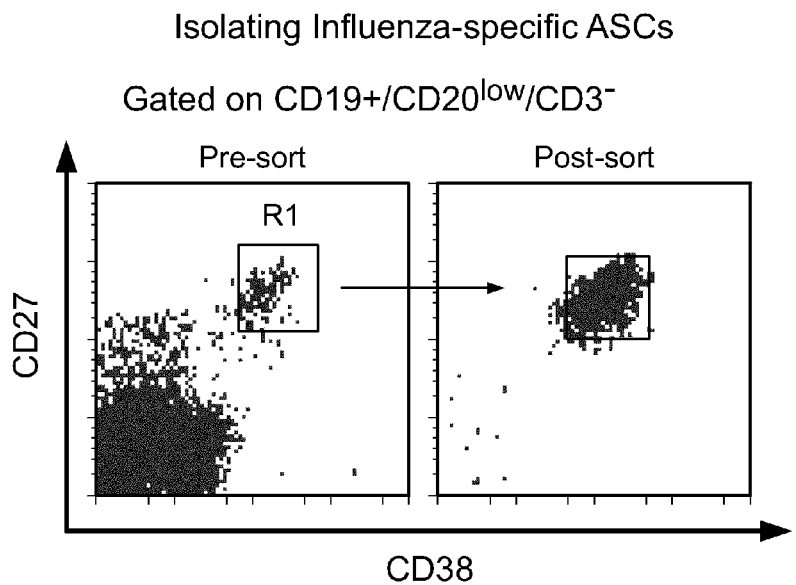
Figure 5A:
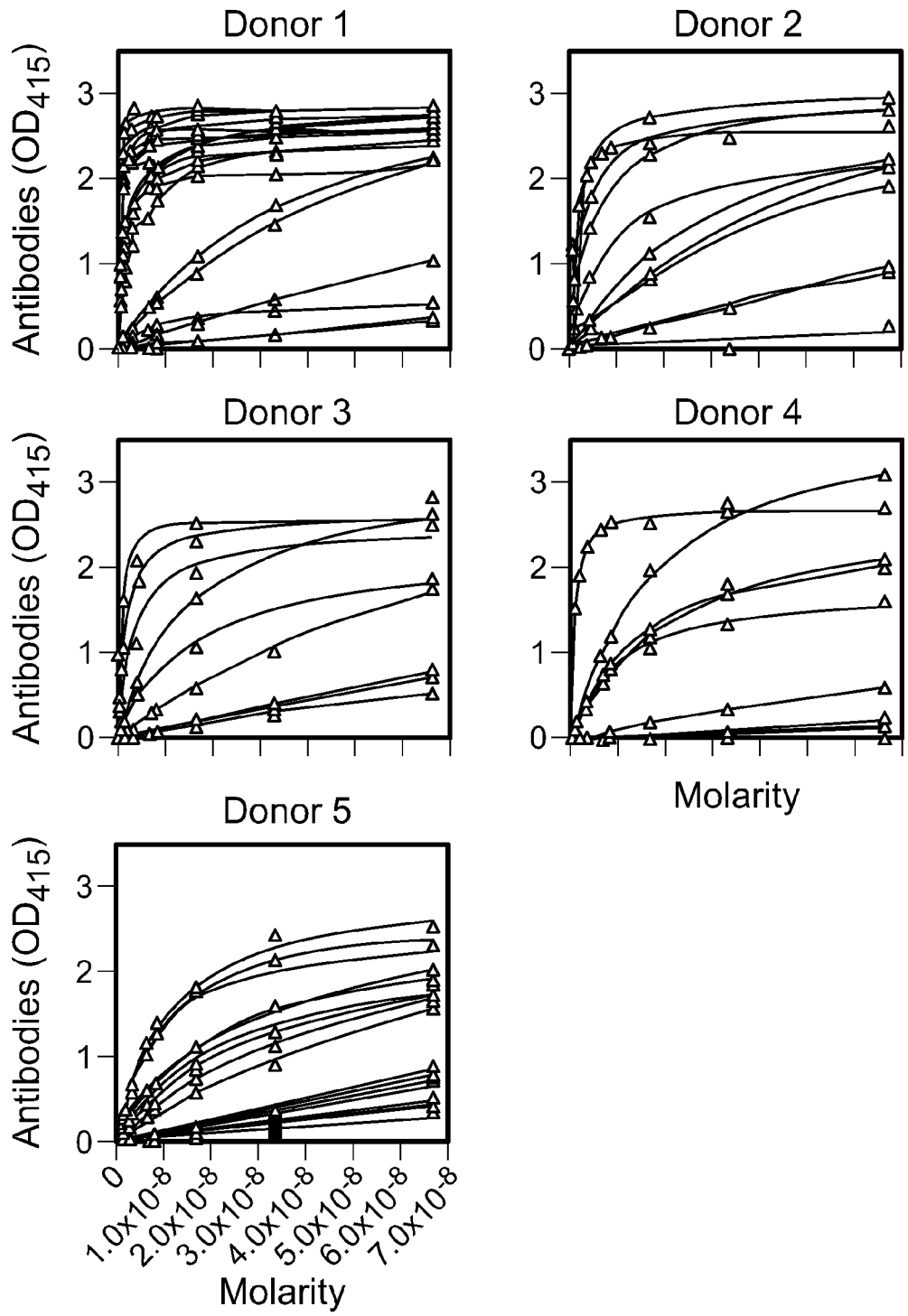
FIGS. 5A-5C: High-affinity mAbs generated from single influenza-specific ASCs. a, Recombinant mAbs from day-7 IgG anti-influenza ASCs (FIG. 8B) bind to a mixture of the three influenza vaccine strain virions with high affinity. In total, 71% of the ASC antibodies bound either native antigens of influenza viruses freshly grown in eggs (53/86, 62%), or to antigens within the vaccine only (8/86, 9%, not shown). Antibodies from each of the five donors were influenza specific (by donor, 34, 13, 11, 15 and 21 antibodies were generated, of which 45-85% were influenza specific). Individual antibody strain specificities are shown in FIG. 7 and FIG. 9B. None of 86 naive B-cell antibodies bound influenza. (C) Analysis by immunoprecipitation and western blot (FIG. 8) identified the specific viral antigens bound. Haemagglutination assays identified those antibodies that were inhibiting (FIG. 7 and Methods). HA, haemagglutinin; NA, neuramininidase; NP, nuclear protein; M, matrix protein.

Generation and Characterization of Antibodies from Subjects Immunized with Influenza Vaccine In this Example, healthy volunteers received influenza vaccine formulations (Fluzone, Aventis Pasteur, 2005/6, or Fluvirin, Chiron, 2006/7). Antibodies were produced from these immunized volunteers. The dynamics and magnitude of the human anti-influenza response studies by analyzing the frequency of ASCs and memory B cells in a time course after vaccination with influenza vaccine. The ASC response was quite transient, peaking at approximately day 7 and returning to barely detectable levels by day 14 after vaccination (FIGS. 3A and 3B). The frequency of influenza-specific ASCs averaged 6.4% (about 2,500 ASCs per millilitre of blood) at day 7, and accounted for up to 16% of all B cells (range for ten donors: 1.1-16%, FIG. 3B). Also, most of these ASCs were generated during the vaccination response as almost all ASCs expressed the protein bound by the Ki-67 antibody, indicating recent proliferation, and most expressed homogenously high levels of human leukocyte antigen DR (HLA-DR) (FIG. 3C). Importantly, analysis of IgG-secreting ASCs isolated by cell sorting at day 7 post-immunization demonstrated that most were influenza vaccine-specific (ranging from 20% to 85%, average 70%; FIG. 3D). The ASCs were mainly IgG positive, with minor components of IgA and IgM-positive cells, suggesting an origin from the memory B-cell compartment. The memory B-cell response was also quantified. Increasing from low levels before vaccination, influenza-specific memory B cells peaked a week after the ASC response at 14-28 days after vaccination and averaged 8.2% of the IgG1 memory B cells, or about 1% of all B cells (FIG. 5E). We conclude that influenza vaccination results in a massive burst of IgG1 ASCs that are predominantly influenza reactive and peak at approximately day 7 post-immunization.

Figure 8A:
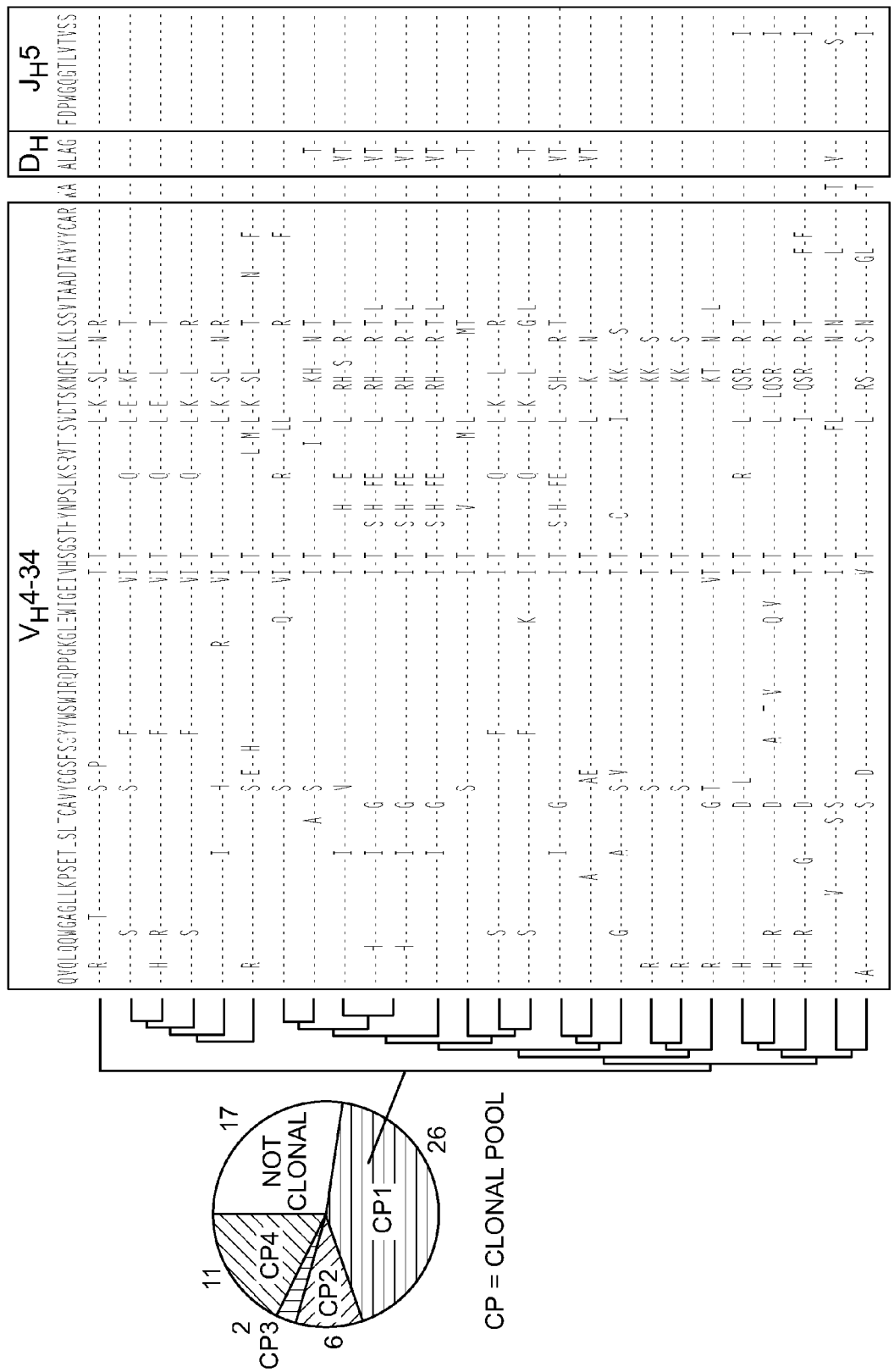
FIGS. 8A-8C: (A) Determination of total frequency of clonally-related B cells. Each slice of the pie chart (left panel) represents a unique clonal expansion or the proportion of variable gene sequences from a single donor that were derived from particular progenitor B cells (clonal pool). Each clonal pool represents variable genes that share identical VH, D, and JH genes and junctions between these genes, but can be distinguished based on the accumulation of somatic mutations. Right panel: the phylogenic tree and individual amino acid sequences of one of the clonal pools (CPI). ELISPOT assays demonstrated that 1,300 anti-influenza ASCs were detectable in each ml of blood from this donor at day 7, totaling ~5% of all B cells. Therefore in each ml of blood, there were over 400 ASCs, or 1.5% of all B cells derived from this single clonal expansion (totaling ~2,000,000 clonal progeny in the blood of that person). Interestingly, analysis of 86 variable genes from this one clonal expansion found that most (85%) differed by individual somatic mutations, and thus mutation and expansion likely occurred together and de novo after vaccination. (B) Strategy for generating recombinant mAbs from the VH and VK genes of single cell-sorted influenza specific ASCs. Single day 7 ASC cells (CD19+/CD20$_{lo}$/CD3−/CD27$_{hi}$/CD38$_{hi}$) were sorted and the VH and Vκ genes amplified by a one step reverse transcription and PCR with primers to the variable gene leader region and constant regions. The identified light and heavy chain genes were cloned into an expression vector and then cotransfected into 293 cells. (C) Time line for the above procedure. This protocol can progress from immunization to production of multiple human mAbs in less than thirty days.

The rapid accumulation of ASCs suggests that the response could be highly clonal in nature, limiting the early influenza response. Some clonal activation of ASCs occurs after tetanus vaccination. We therefore analyzed the immunoglobulin repertoire breadth (that is, the variable genes and junctional diversity) of the influenza-specific ASCs. Influenza vaccination caused a surprisingly pauci-clonal response, with some donors being dominated by the progeny of only a few expanded B-cell clones (FIG. 4A and FIG. 8A).

Figure 4C:
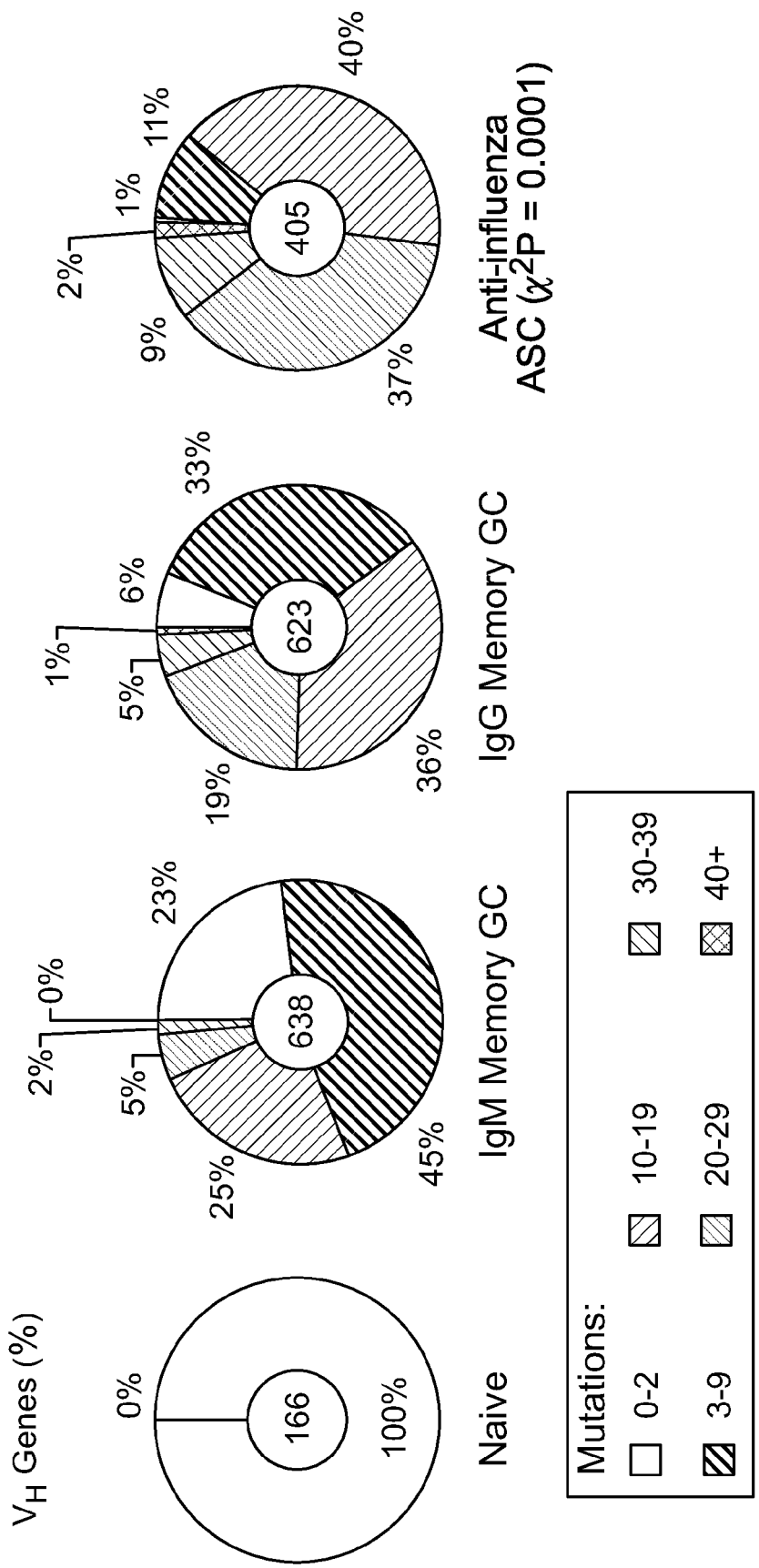

Clonal expansions accounted for 43% of the ASC variable regions from the 14 immunized donors, including three with over 70% clonality (FIG. 4A). In stark contrast, based on VH regions sequenced earlier in a comparable fashion, naive and memory B cells (IgM or IgG) isolated from blood were rarely or never clonal, whereas for tonsillar B cells only 10% of IgM and 12% of IgG germinal centre and memory cells were clonally related. Immunoglobulin variable gene somatic hypermutation allows for the generation of high-affinity antibodies. Surprisingly, the influenza-specific ASCs had accumulated more somatic mutations than any normal population of B cells. Considering the various donors (FIG. 4B), the ASCs averaged 19.4+/−3.5 $V_H$ gene mutations, which is greater than that of germinal centre or memory B cells which average 13.6+/−4.8 mutations for IgG or 8.4+/−3.8 mutations for IgM. A surprising 11% (41/405) of the ASC VH gene segments have more than 30 of 300 (or about 10%) of the total nucleotides altered (FIG. 4C). A preference for complementarity-determining region replacement mutations suggests that the ASCs were functionally selected (FIG. 7). These observations suggest the origin of the anti-influenza ASCs is predominantly memory B cells that probably accumulated new mutations on this and on previous rounds of activation.

Figure 5B:
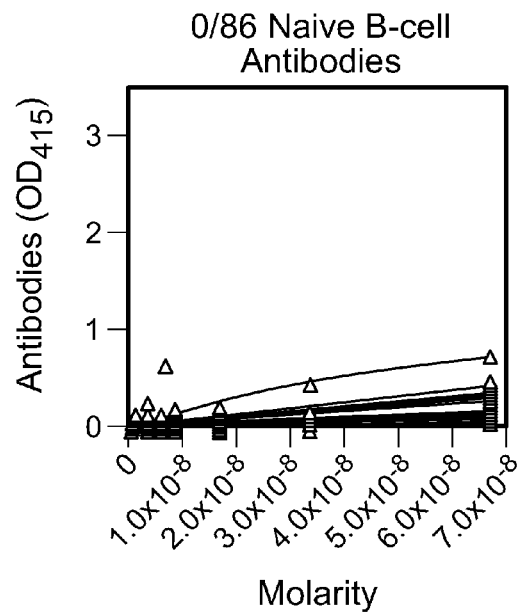
Figure 5C:
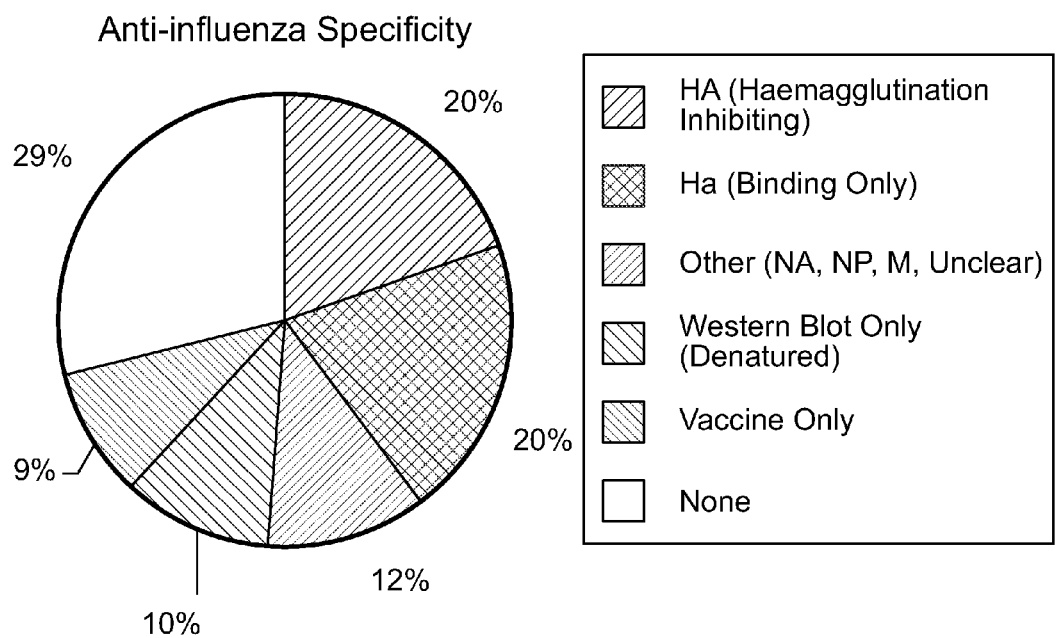
Figure 6C:
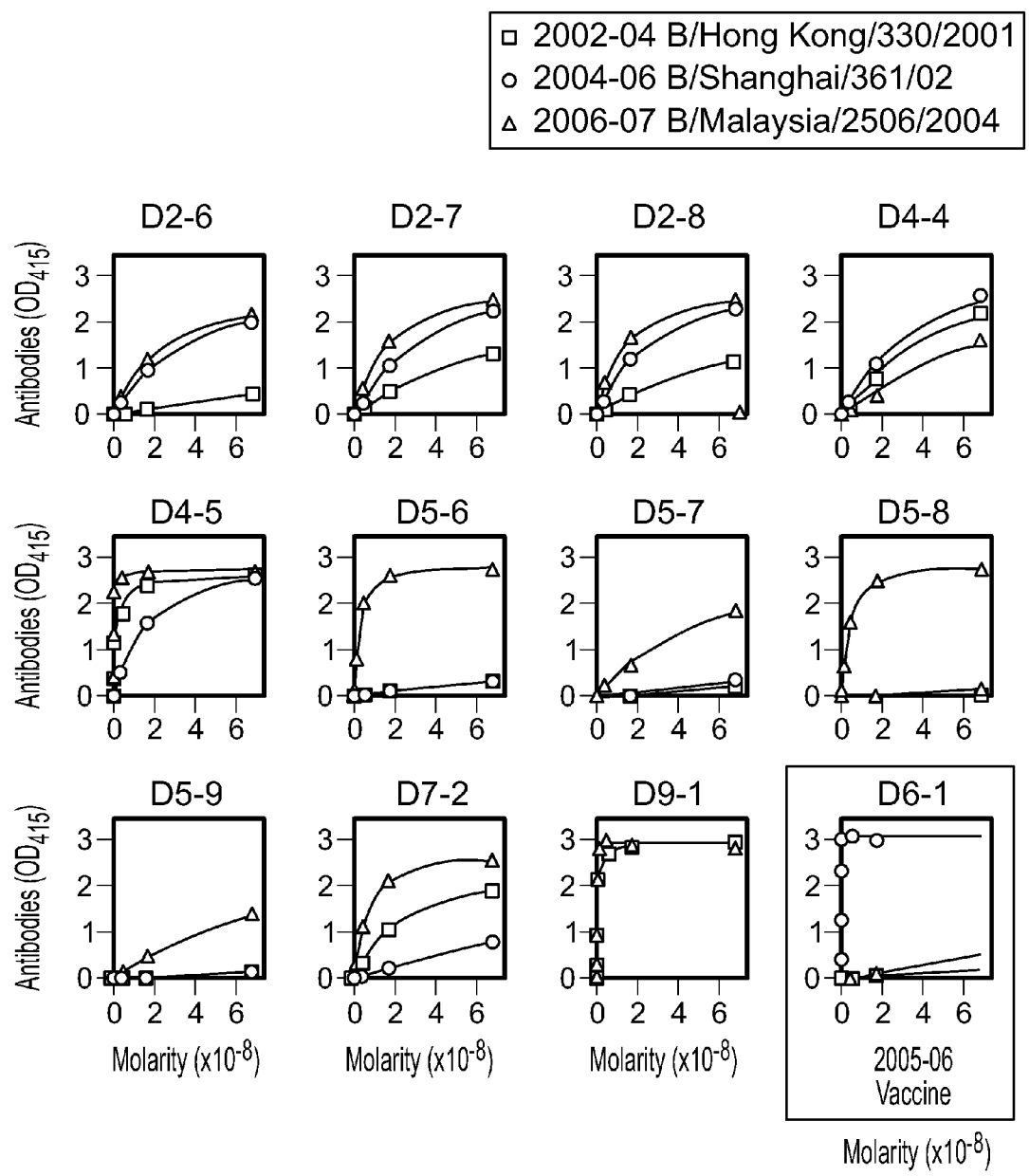
Figure 8B:
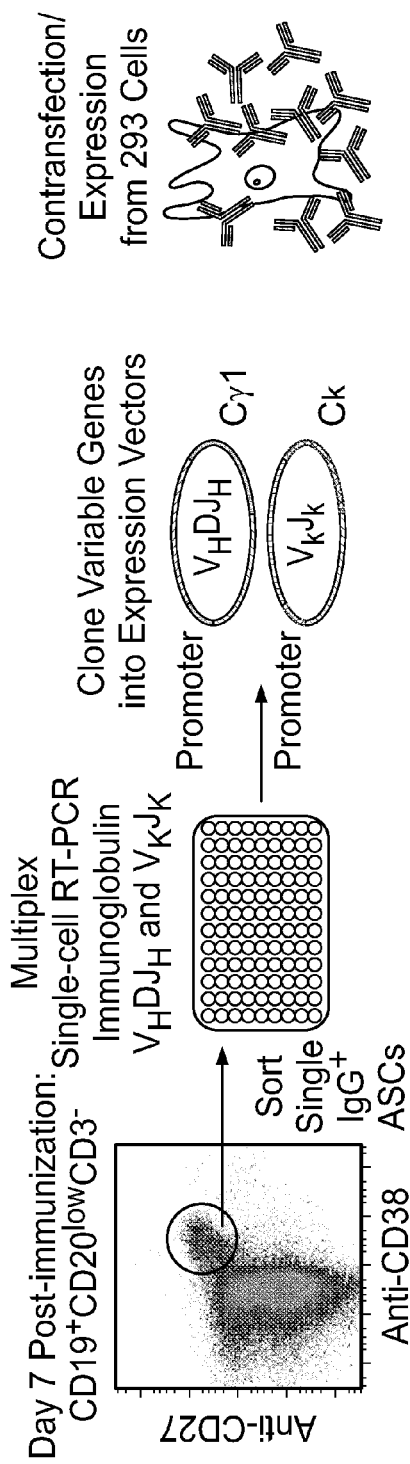
Figure 8C:
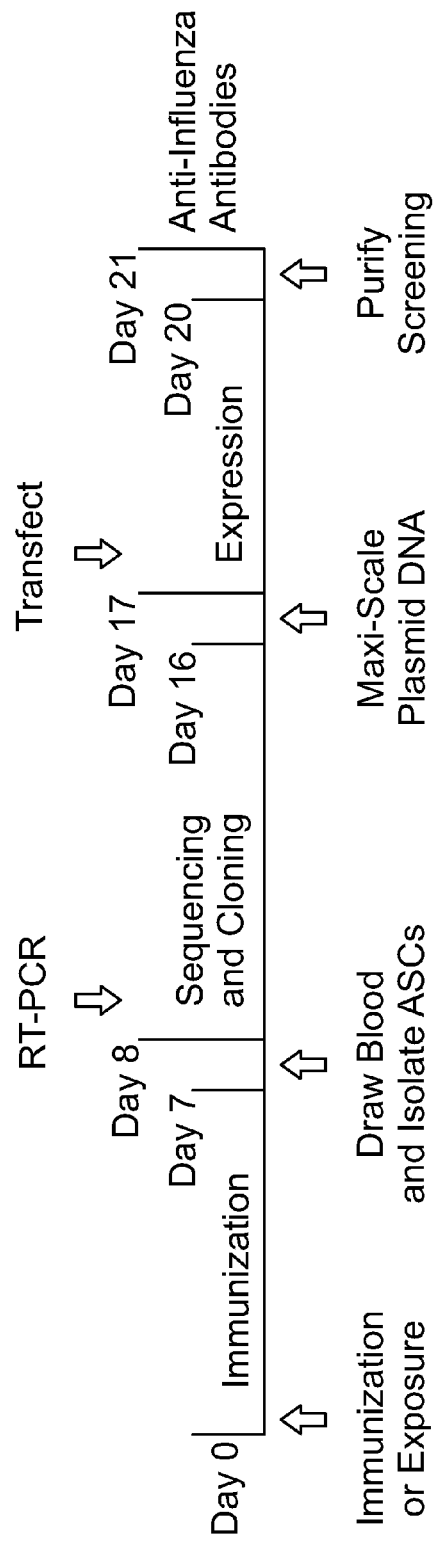
Figure 9:
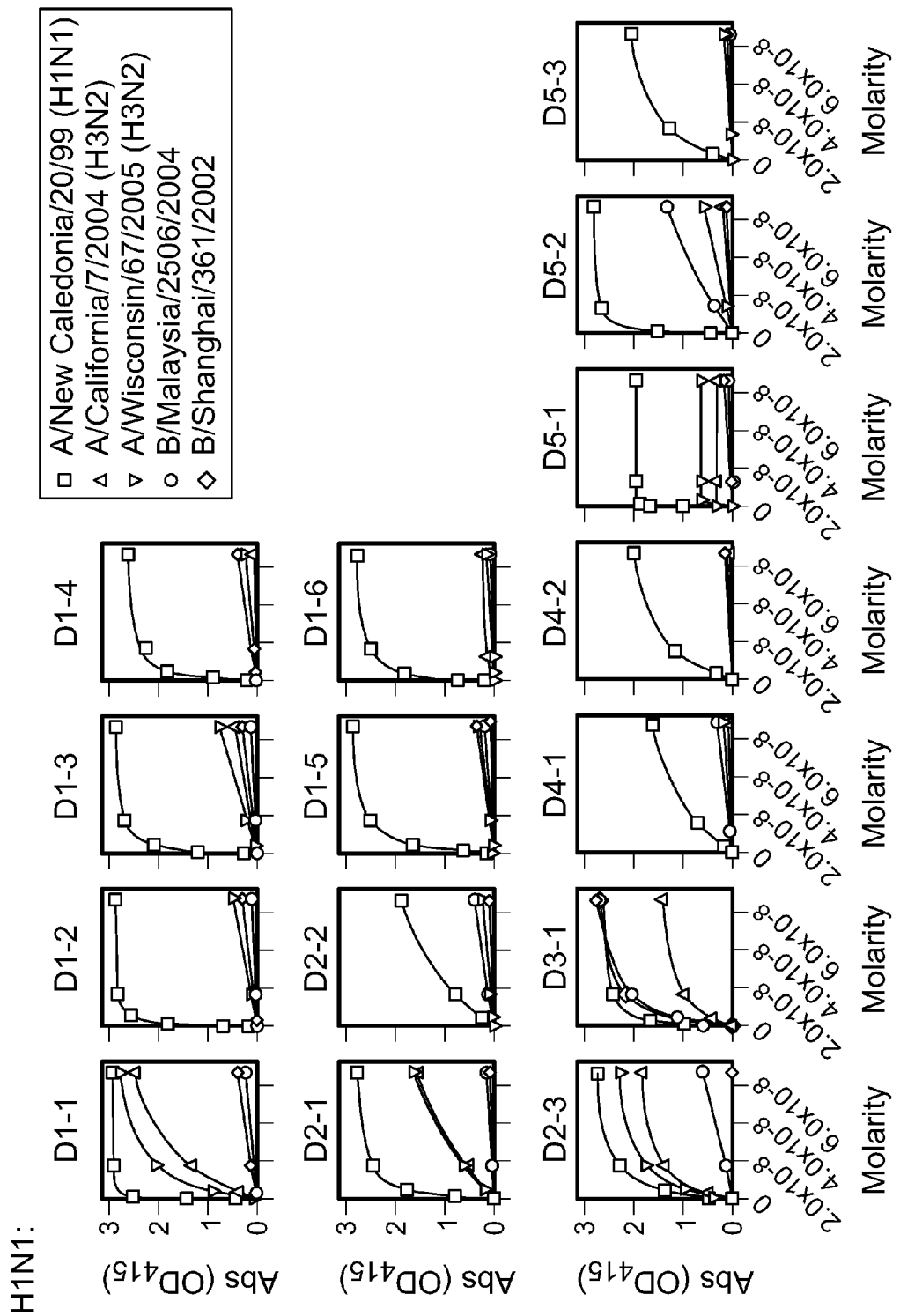
FIG. 9: Binding curves of the influenza-specific antibodies to the five different strains of influenza. Curves are grouped by virus type to which the particular antibody had the greatest Kd. Note that heterosubtypic cross-reactivity (to both A and B strains) was limited to low affinity interactions and HAI activity was not evident for more than one type of hemagglutinin for any particular antibody (For example, antibodies that inhibited H2 could not inhibit H1 or B strain hemagglutinin). We suspect these antibodies may bind common nonprotein epitopes (such as glycans) or that they are somewhat polyreactive.
Figure 9:
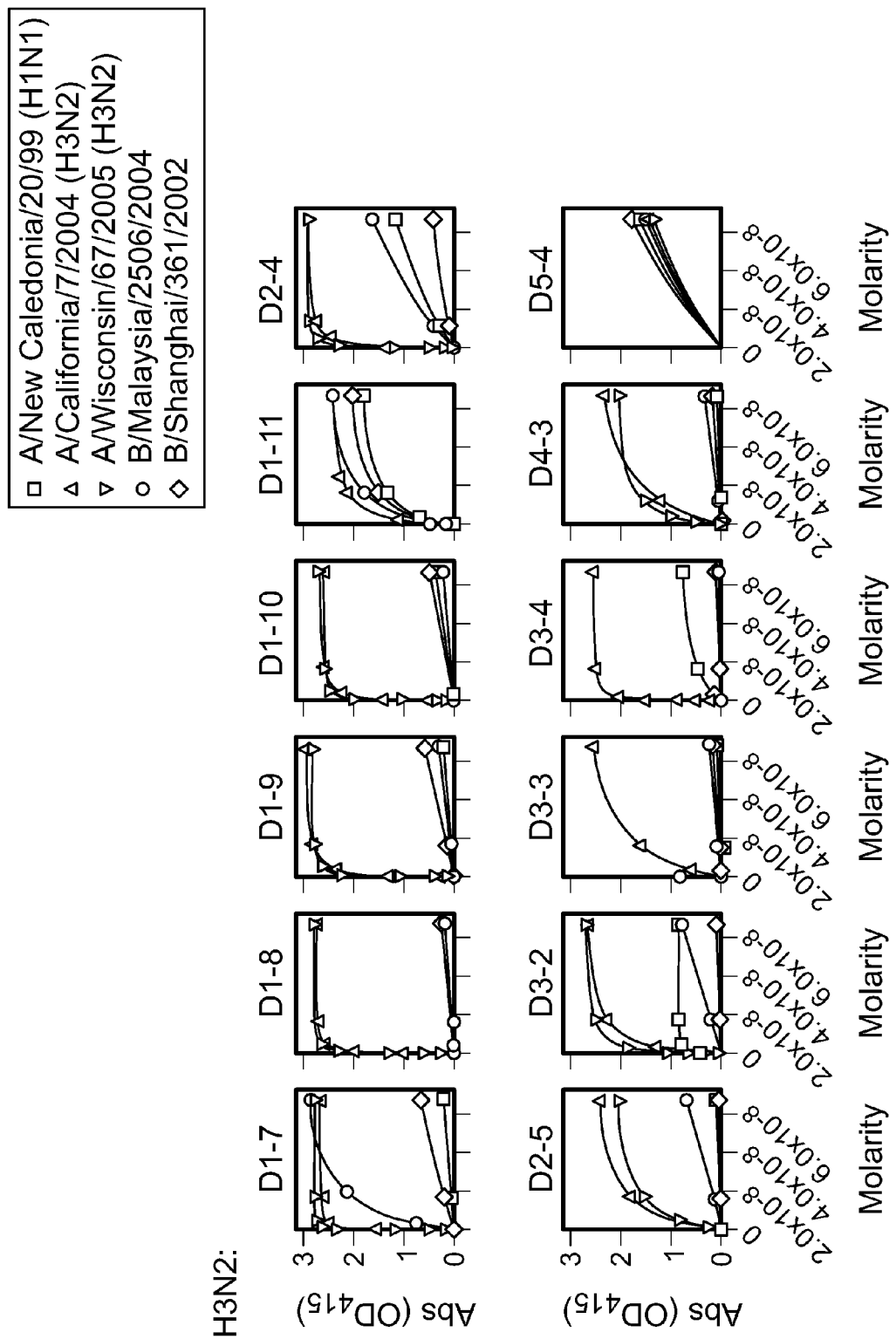
Figure 9:
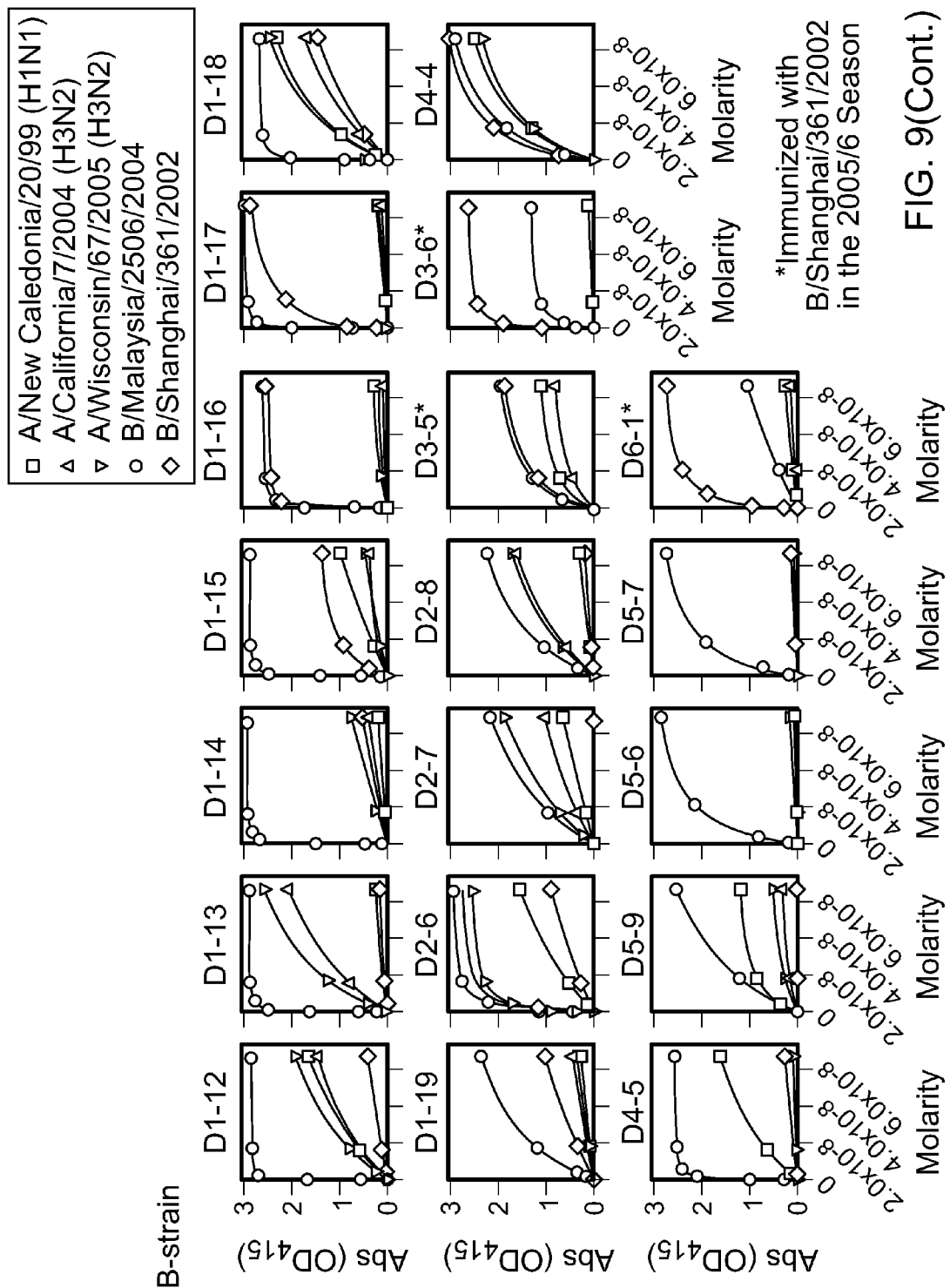
Figure 10A:
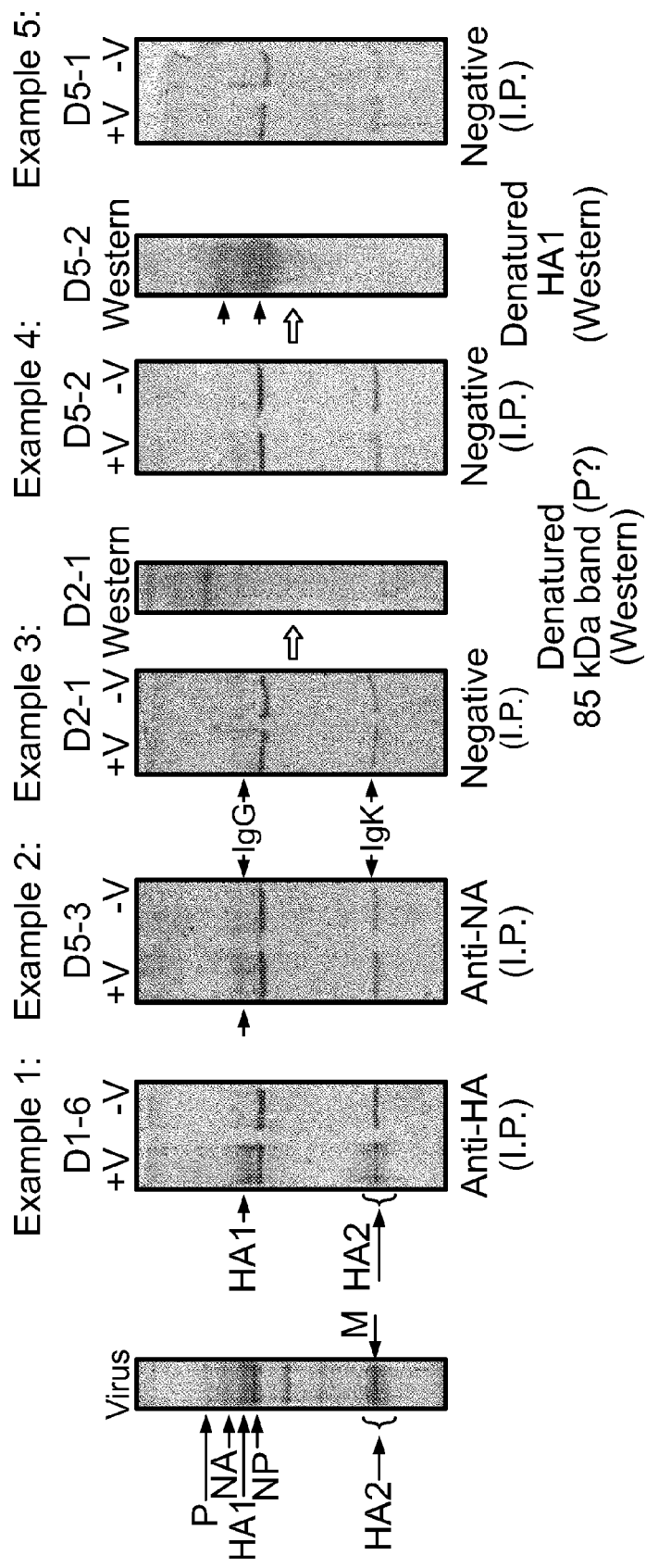
Figure 10B:
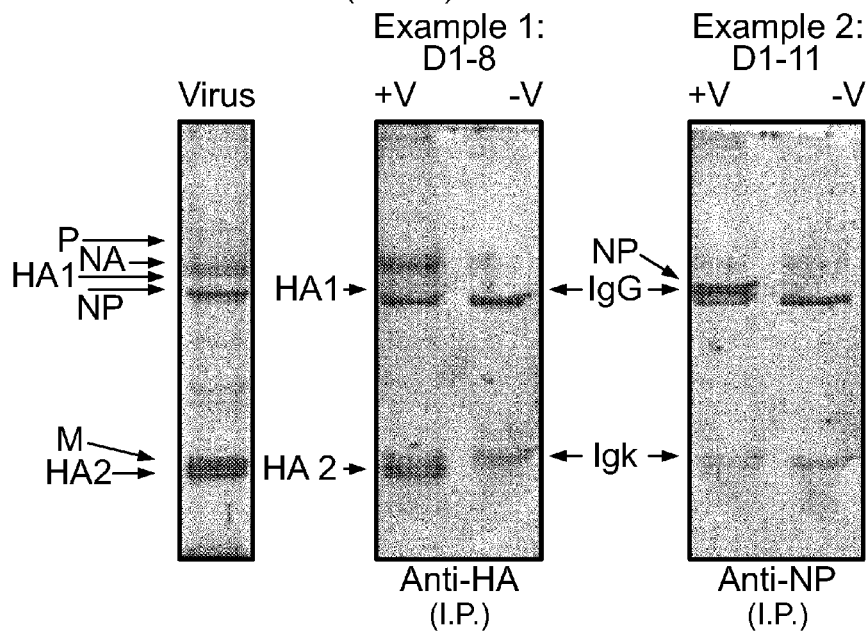
Figure 10C:
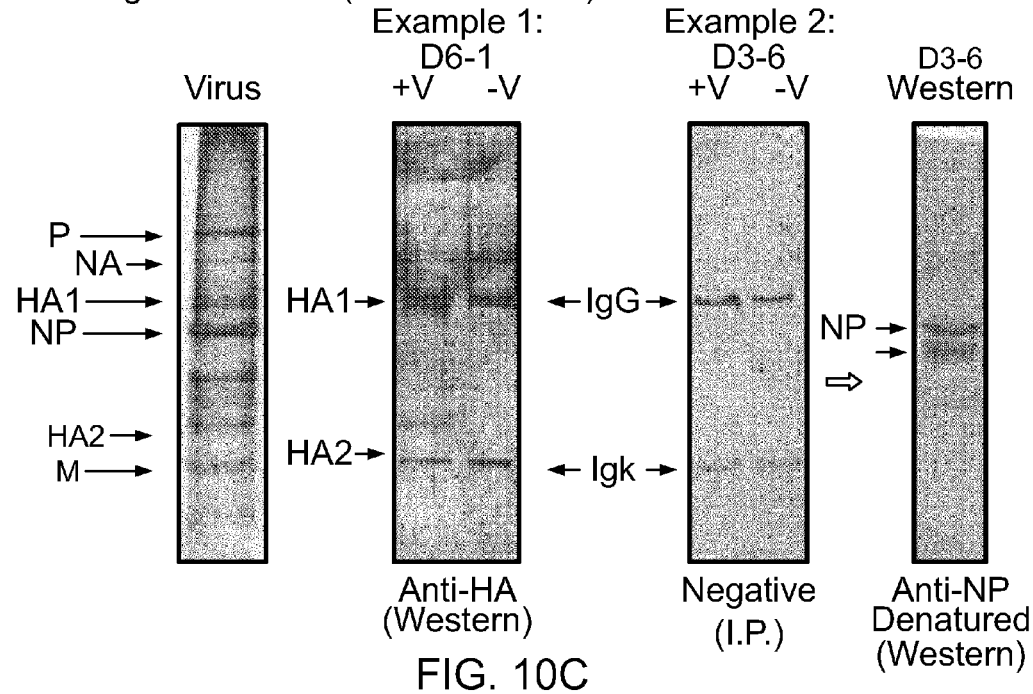
Figure 10D:
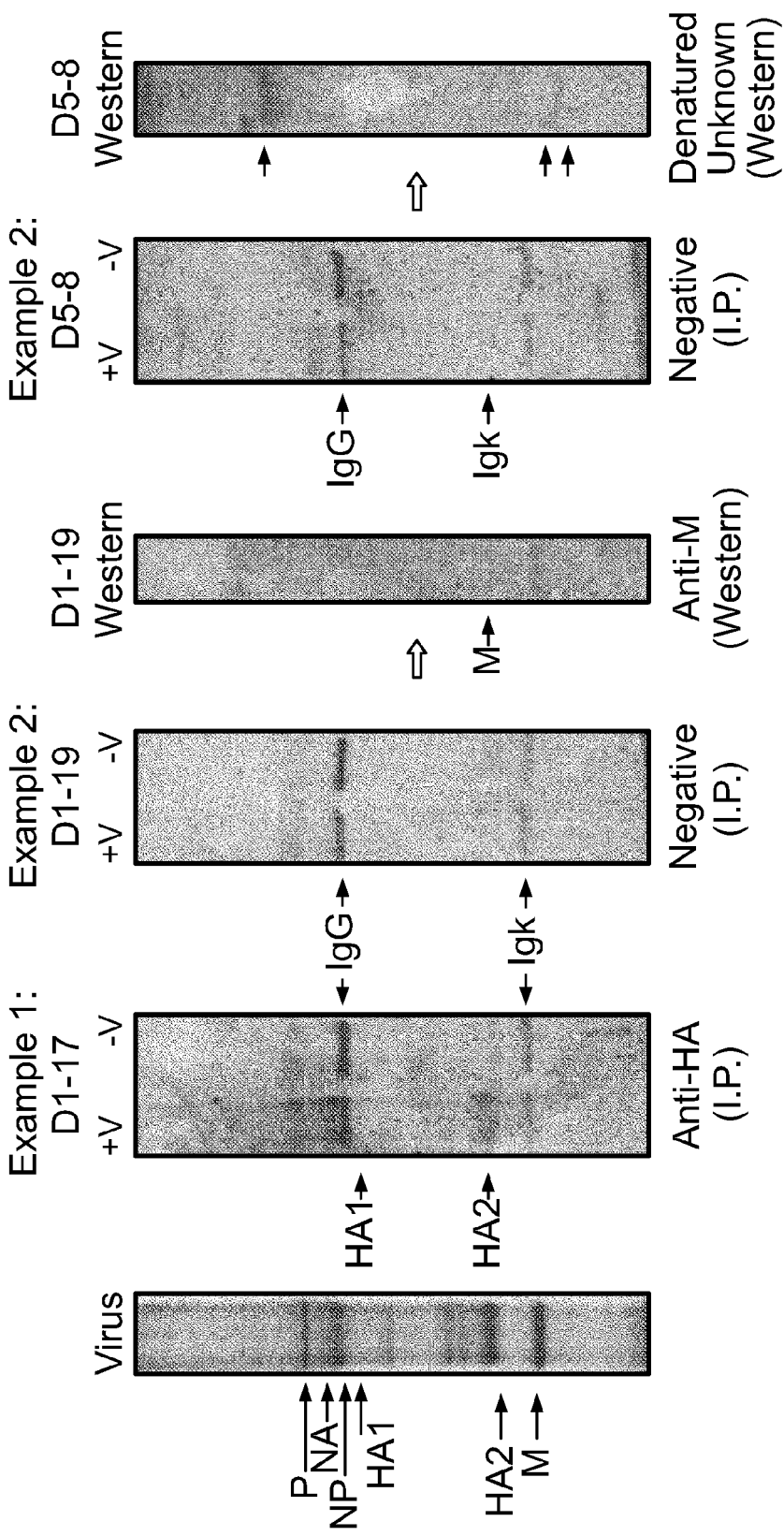
Figure 11:
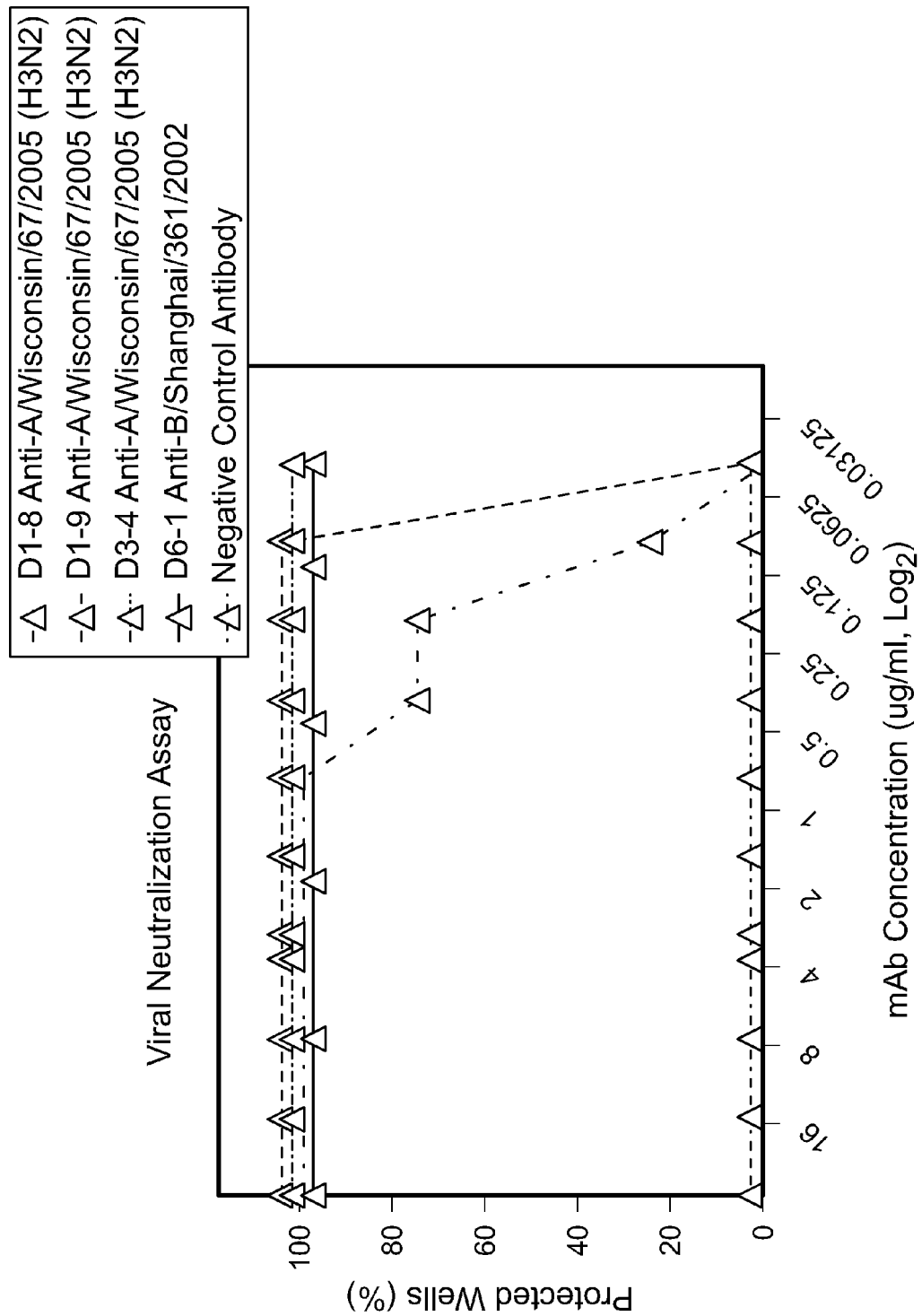

It is not known how often the ASCs that are induced by vaccination produce high-affinity antibodies against influenza. Immunoglobulin variable region genes from ASCs can be used to express specific antibodies. We therefore used the variable gene transcripts of isolated single ASCs to express recombinant mAbs in the human 293 cell line (FIG. 8B). The ASCs of five donors were isolated at day 7 post-vaccination. From these, 71% (61/86) of the antibodies bound with high affinity to either native antigens of the influenza vaccine strains (53/86, 61%) or to components of the vaccine only (8/86, 9%) (FIG. 5, FIG. 7 and FIG. 9). We suspect that the epitopes found only in the vaccine are exposed on the fixed virions or are from added preservatives. In comparison, none of the 86 mAbs generated from naive B cells (FIG. 5D) and only one of 54 antibodies from random IgG memory B cells bound to the influenza vaccine strains with appreciable affinity. The antibodies produced from the influenza-specific ASCs bound to any of the three vaccine components with similar frequency (FIG. 9). Analysis of viral antigen specificity by immunoprecipitation and western blot (FIG. 5) found that 60% of the influenza-reactive antibodies bound to haemagglutinin, of which half were haemagglutination inhibiting (HAI) (FIG. 5C and FIG. 7). Twelve percent of the antibodies bound to neuraminidase or to other minor components of the vaccine likely residual to the purification of haemagglutinin and neuraminidase during vaccine production. Ten percent of the antibodies did not precipitate native antigens and bound only to epitopes on denatured viral proteins detectable by western blot. Importantly, each of three representative HAI+ antibodies against influenza-A (anti-H3N2) and one against influenza-B from the day-7 ASCs (FIG. 7, bold) were found to neutralize viral infection of Madin-Darby canine kidney (MDCK) cells in vitro (each neutralized virus at less than 1 µg/ml antibody, FIG. 11). In conclusion, after influenza vaccination, early ASCs produce functional antibodies that bind with high affinity and likely provide early protection. Although most of the ASCs arise only after vaccination (FIG. 3A), 29% of the antibodies generated did not detectably bind to the influenza strains or whole vaccine (FIG. 6c). Possible causes include errors introduced by the reverse-transcription polymerase chain reaction (RT-PCR) steps (though PCR errors were rare, FIG. 9), targeting of non-viral or denatured components of the vaccine or antigens only evident physiologically, bystander activation of non-specific memory cells, or displacement of non-specific plasma cells from the bone marrow. The last possibility is unlikely as expression of HLA-DR13 and Ki-67 (FIG. 3C) by the ASCs suggests they were newly generated. The long-held theory of OAS suggests that new influenza variants will evade surveillance when memory B cells reactive to previous viral strains dominate the response. To consider the impact of OAS directly, we compared the relative affinity with either the current B strain virus (B/Malaysia/2506/2004) or with the two previous ones (B/Shanghai/361/2002 or B/Hong Kong/33/2001) (FIG. 6A and FIG. 6B). In the 2006/7 season, antibodies were analysed from five donors who had also been vaccinated in the 2005/6 season and one in 1991, so that reactive memory cells should have been readily available for an OAS response. Importantly, each of the 19 anti-B strain antibodies bound to the new B strain with equal, and in most cases with greater, affinity than the previous vaccine strains (FIG. 6C and FIG. 9). This adaptation occurred despite the 10% or less difference of the haemagglutinin sequence of the 2006/7 B strain from those used in previous vaccines. Although previous exposure to B/Malaysia/2506/2004 cannot be entirely excluded, there was no history of exposure, and pre-vaccination serum titres of antibody against B/Malaysia/2506/2004 were not above background levels (data not shown). Thus we conclude that even for the earliest detectable influenza specific B cells after vaccination, the ASCs, OAS does not limit reactivity to newly introduced influenza strains. In conclusion, we show that after influenza vaccination we can isolate an almost entirely antigen-specific population of ASCs that comprise about 5% of all blood-borne B cells.

Our findings help to resolve a major, long-standing obstacle in the field of medicine: the rapid production of fully human mAbs. Antibody or serum therapy has been demonstrated to treat a plethora of diseases effectively, but it is not widely used because sometimes fatal anaphylactic responses and serum sickness are common. These obstacles can only be overcome by using fully human mAbs. Our findings demonstrate that we can now generate human mAbs from the antigen-specific ASCs directly, and within only weeks of vaccination (FIG. 3C). With a modern resurgence of interest in monoclonal antibody therapy, we anticipate that antibodies produced from post-vaccination ASCs will generate substantial advances for the treatment of infectious diseases. Conventional wisdom holds that the level of pre-formed antibody is the main correlate of protection against influenza virus. However, our results, showing the rapidity of the antibody response after vaccination and the high affinity of the antibodies produced, strongly suggest that the recall response could also play a role in protective immunity. This antibody would not, of course, prevent initial infection but could play a crucial role in preventing the spread of virus and bringing about faster resolution of the infection. This notion is supported by our finding that OAS was not a significant aspect of the memory response, as the antibodies produced were highly specific to the immunizing antigen.

Methods

Cell and serum isolation All studies were pre-approved by the institutional review boards of Emory University School of Medicine and the Oklahoma Medical Research Foundation. Healthy volunteers received influenza vaccine formulations (Fluzone, Aventis Pasteur, 2005/6, or Fluvirin, Chiron, 2006/7). PBMCs were isolated using Vacutainer tubes (Becton Dickinson) or lymphoprep gradient (CellGro), washed and re-suspended in supplemented culture media or PBS. Plasma was heat inactivated.

ELISPOT and memory B-cell assays ELISPOT and memory assays were aspreviously described. Total IgG secreting or influenza-specific ASCs were detected using 1/20 diluted influenza vaccine in PBS (as above) or with goat anti-human Ig (Caltag). Dilutions of washed PBMCs incubated in supplemented RPMI medium for 2 h were incubated in ELISPOT plates for 6 h. After washing the plates, ASC antibody was detected with anti-huIgG-biotin (Caltag) and avidin-D-HRP (Vector Laboratories) and developed with AEC substrate (Sigma) before analysis on an ELISPOT counter (Cellular Technologies Ltd.). Memory cells were detected by incubating PBMCs at $5\times10^5$ cells per millilitre in R-10 supplemented with pokeweed mitogen extract, phosphothiolated CpG ODN-200626 and Staphylococcus Aureus Cowan (Sigma). After culture for six days, the cells were washed and quantified by ELISPOT.

Flow cytometry and cell sorting Flow cytometry was performed on whole blood after lysis of erythrocytes. Mostly Pharmingen antibodies were used for quantifying ASC or memory cells (FIG. 1) except anti-CD27-APC (ebiosciences) and goat anti-huIgG-FITC (Southern Biotechnologies). For single-cell analysis and production of mAbs, antibodies used included anti-CD3-FITC, anti-CD20-FITC, anti-CD38-APC-Cy5.5, anti-CD27-PE, anti-IgG-Alexa-647 and anti-CD19-PE-Alexa 610 from Caltag, plus anti-IgD-biotin and strepavidin-Pe-Cy7 (Pharmingen). ASCs were gated as IgG+/IgD–/CD19+/CD3–/CD$_{20}$low/CD27high/CD38high. All other cell types were isolated as previously described. Cytometry data was analyzed using FlowJo software.

Single-cell RT-PCR and PCR of antibody variable region genes As detailed below, single B cells were sorted into 96-well PCR plates containing RNase inhibitor (Promega). VH and Vk genes from each cell were amplified by RT-PCR and nested PCR reactions using cocktails of primers as previously described then sequenced. To generate recombinant antibodies, restriction sites were incorporated by PCR with primers to the particular variable and junctional genes. RT-PCR of bulk RNA to analyse V genes was as previously described.

Analysis of clonality and somatic mutations of variable region genes To quantify clonality, variable genes were randomly sequenced from the bulk RNA of ASCs from ten donors (by donor, n=22, 47, 49, 12, 16, 19, 36, 25, 34 and 63) and verified by single-cell RT-PCR analysis of ASCs from four donors (n=65, 37, 30 and 50). Naive, memory and germinal-centre cell variable gene libraries included the following VH gene n values: blood naive (by donor, n=61, 24, 15, 14 and 24), blood IgM memory (n528, 17, 27, 11, 23, 12, 29 and 20), blood IgG memory (n=23, 18, 18, 17, 22 and 21), tonsillar naive B cells (n=125, 32, 16, 22, 32, 23, 46 and 81), tonsillar IgM and germinal centre/memory (n550, 42, 35, 16, 60, 15, 50, 25, 39, 19, 55 and 58 VH genes) and tonsillar IgG germinal centre/memory (n=113, 25, 14, 40, 12, 41, 11, 23, 18, 51, 15, 54 and 69). Then values for analysis of somatic hypermutation included: anti-influenza ASCs from 11 donors (n=63, 18, 33, 46, 49, 11, 36, 11, 30, 35, 25); IgG germinal centre/memory cells from 14 donors (n=110, 37, 19, 28, 174, 40, 25, 15, 21, 18, 22, 24, 19, 71); IgM germinal centre/memory from 17 donors (n=56, 158, 18, 91, 17, 10, 16, 30, 19, 28, 11, 36, 29, 13, 22, 20, 64); and naive cells from six donors (n=18, 42, 21, 34, 15, 36). Background mutation rates were insignificant Recombinant monoclonal antibody expression and analysis All assays are further detailed below. VH or Vk genes amplified from each single cell were cloned into IgG1 or Igk expression vectors as previously described. Heavy- and light-chain plasmids were co-transfected into the 293A cell line for expression, and antibodies purified with protein A sepharose. The influenza virus strains used for ELISA or HAI were freshly grown in eggs and purified by standard methods and included: A/New Caledonia/20/9(H1N1), A/California/7/2004 (H3N2) for 2005/6 or A/Wisconsin/67/2005 (H3N2) for 2006/7, and B/Shanghai/361/2002-like for 2006/2007 or B/Malaysia/2506/2004 for 2006/7. After ELISA screening with a cocktail of all influenza strains and 1/20 dilutions of the vaccines, the affinity and specificity of binding-positive mAbs were determined with the individual influenza viruses. ELISA affinities were calculated by nonlinear regression analysis of curves from eight dilutions of antibody (10-0.125 μg/ml) using GraphPad Prism. Influenza-neutralizing activity was detected as inhibition of MDCK cell death by 50% tissue culture infectious doses of A/Wisconsin/67/2005 or B/Shanghai/361/2002 based on the protocol of the World Health Organization manual.

Immunoprecipitation and western blot analyses. All assays are further detailed in the below. For immunoprecipitation, 8 haemagglutinin units (HAU) of virus were lysed and incubated with 10 mgml21 of mAb before purification with Protein A-Sepharose (Pierce). mAb was eluted from the protein-A by boiling in Laemmli buffer (Bio-Rad) and analysed on 12% Tris-glycine polyacrylamide gels. Protein was detected by staining the gels with sypro-orange (Invitrogen). For western blots, 8 HAU of virus was diluted and boiled in denaturing/reducing sample buffer, then run on denaturing polyacrylamide gels (as above) followed by electrophoretic transfer to nitrocellulose membranes. The membranes were incubated with each antibody at 5 μg/ml, detected with HRP anti-human IgG (Jackson Immunoresearch) and developed with ECL plus reagent (GE Healthcare). IP gels and western blot membranes were analysed using a STORM840 system (Molecular Dynamics).

Statistics. Statistical analyses (described in context) were performed using GraphPad Prism: frequencies of clonal relatedness and somatic mutation were compared by non-paired, two-tailed Student's t-tests; x2 tests compared summed mutation frequencies.

Memory B Cell Assay

Memory B cell assays were essentially done as previously described 14,25. In brief, PBMC were plated in 24-well dishes at $5\times10^5$ cells/well in R-10 supplemented with an optimized mix of polyclonal mitogens: pokeweed mitogen extract (PWM) (made in house), phosphothiolated CpG ODN-200626, and Staphylococcus Aureus, Cowan (SAC) (Sigma). 7 wells were cultured per individual for 6 days with 7 non-stimulated wells as a negative control. The stimulated cells were harvested, washed extensively and assayed using the ELISPOT assay described above. Data is represented as the percentage of IgG secreting influenza-specific cells over the total number of IgG secreting cells. Estimation of the total frequency of memory B cells that were influenza specific following vaccination was based on the finding that on average 12% of blood B cells from 25 healthy normal adults are IgG memory cells (CD19+CD27+IgG+).

Hemagglutination inhibition assay HAI titers were determined for the three viruses making up the 05-06 vaccine (A/New Caledonia/20/99 (H1N1), A/California/7/2004 (H3N2) and B/Shanghai/361/2002; viruses kindly provided by the CDC) as previously described27. Briefly, serum samples were treated with receptor destroying enzyme (RDE; Denka Seiken Co.) by adding of 1 part serum to 3 parts RDE and incubating at 37° C. overnight. The following morning, the RDE was inactivated by incubating the samples at 56° C. for one hour. The samples were then serially diluted with PBS in 96 well v-bottom plates and 8 HAU (as determined by incubation with 0.5% turkey RBCs in the absence of serum) of either the H1N1, H3N2, or influenza B virus was added to each well. After 30 minutes at room temperature, 50 ul of 0.5% turkey RBCs (Rockland Immunochemicals) suspended in PBS with 0.5% BSA was added to each well and the plates were shaken manually. After an additional 30 minutes at room temperature, the serum titers were read as the reciprocal of the final dilution for which a button was observed. Negative and positive control serums for each virus were used for reference (data not shown; reagents provided by the CDC).

Flow cytometry and cell sorting Flow cytometry analysis was performed on whole blood. Briefly, 300-400 μl blood was incubated with the appropriate antibodies for 30 minutes at room temperature. Red blood cells were then lysed by incubation with FACS lysing Solution (Beckton Dickinson) for 4 minutes at RT. All antibodies used for determining the dynamics of ASC or memory cells production and for bulk variable gene, analyses were purchased from Pharmingen with the following exceptions: CD27 APC (ebiosciences) and goat anti-huIgG FITC (Southern Biotechnologies). For these cell sorting experiments, PBMCs were stained with the appropriate markers and sorted on a FACSVantage. Analysis of data was performed using FlowJo software.

For single cell analysis and production of mAbs, B cells were bulk sorted using a Becton-Dickinson FACS Aria cytometer and then resorted into 96-well PCR plates with a Cytomation MoFlo cytometer fitted with a single-cell sorting apparatus (98-99% purity detected on sort of the single cells). Antibodies used for flow cytometry for these analyses were anti-CD3 and anti-CD20 conjugated to FITC (Caltag), anti-CD38 conjugated to APC-Cy5.5 (Caltag), anti-CD27 conjugated to PE (Caltag), and anti-CD19 conjugated to PE-Alexa 610 (Caltag). In order to improve the efficiency of the single-cell PCR by ensuring only IgG+ cells were sorted, bitoinylated anti-IgD and strepavidin-Pe-Cy7 (Pharmingen) and anti-IgG (Caltag) conjugated to in house to Alexa-647 ((Invitrogen) were used. IgG+IgD− ASCs were gated as CD19+CD3−CD20low and then subgated as CD27high CD38high. Naïve B cells (IgD+CD38−, tonsil, or IgD+CD27−, blood), IgG+ and IgM+ GC cells (CD38+ tonsil) and memory cells (CD38−CD27+ tonsil or CD27+ blood) were isolated.

Single cell RT-PCR and PCR of antibody variable region genes Single B cells were sorted into 96-well PCR plates containing 10 mM Tris-HCL with 40 units/ul of RNase inhibitor (Promega). Plates of single cells were immediately frozen on dry ice and stored at −80 C. VH and Vκ genes from each cell were amplified in a one-step RT-PCR reaction (Qiagen) using a cocktail of sense primers specific for the leader regions and antisense primers to the Cγ constant regions for heavy chains and Cκ for the light chain. One microliter from each RT-PCR reaction was amplified in separate PCR reactions for the individual heavy and light chain gene families using nested primers as previously described15,24. PCR products were then sequenced (ABI 3730 capillary sequencer). When recombinant antibodies were to be generated, upon identification of the variable genes, sense primers unique to the particular variable genes and antisense primers binding the particular junctional genes were used in a new nested PCR reaction with 1 ul of the RT-PCR as template to incorporate restriction sites at the ends of the variable genes for cloning. Variable genes were amplified from bulk RNA of IgG ASC and memory cells or IgM memory cells by RT-PCR using primers specific to the VH3 and VH4 families.

Analysis of Clonality and Somatic Mutations of Variable Region Genes.

Figure 3E:
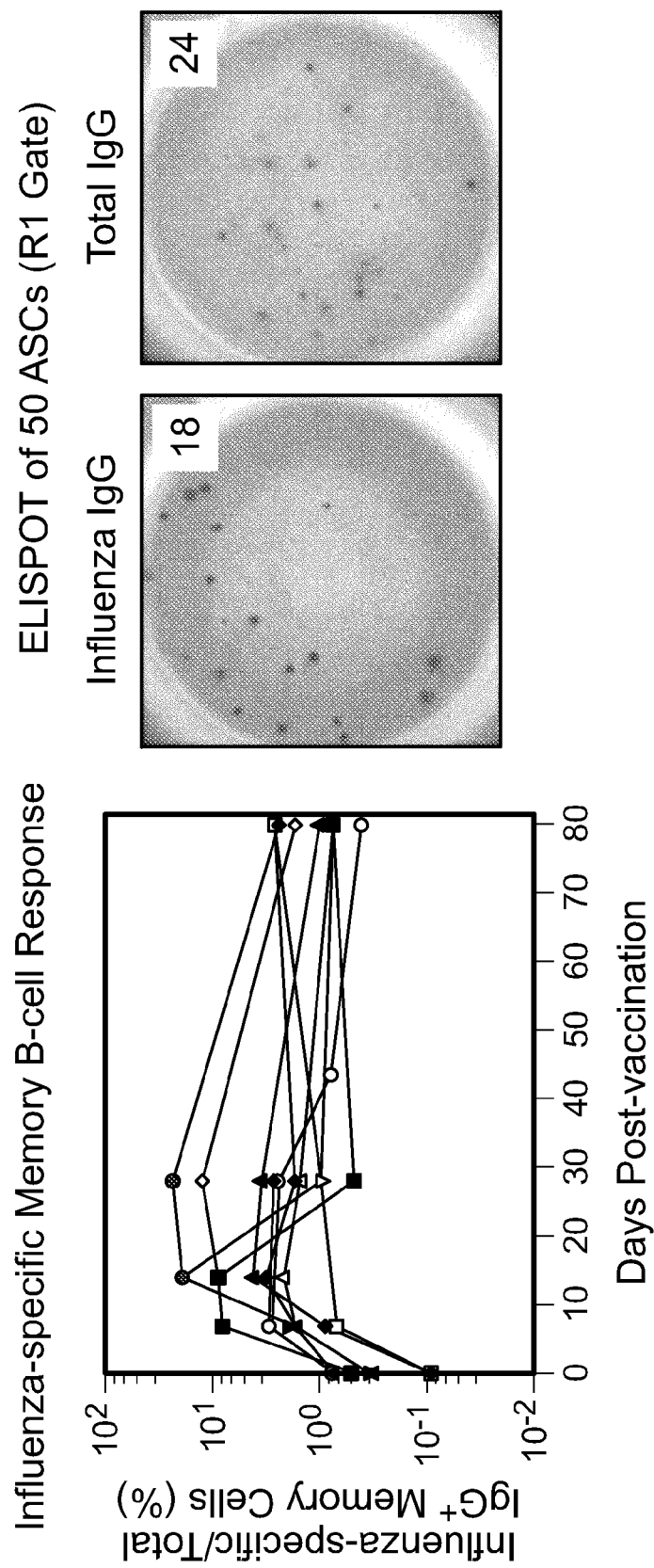

For analysis of clonality, variable genes were randomly cloned and sequenced from the bulk RNA of $10^4$ to $10^5$ ASCs amplified by RT-PCR from 10 donors (by donor, n=22, 47, 49, 12, 16, 19, 36, 25, 34, and 63 VH genes) and verified by single cell RT-PCR analysis of single sorted ASCs from four donors (by donor, n=65, 37, 30, and 50 VH genes). For bulk analysis, VH3 and VH4 family variable genes (representing ⅔s of all antibody heavy chain genes28) were randomly cloned and sequenced, and for the single cell PCR analyses all VH genes were considered. Most clones from the single cell PCR analyses were verified by isolation of similar light chain (Vκ) transcripts from the same cells in a multiplex PCR reaction. All donor ASC samples were verified to be anti-influenza positive by ELISPOT (FIG. 6b) or by production of recombinant mAbs from the single cells (see below). The naïve cell variable gene libraries as well as many of the IgM and IgG GC and memory VH gene libraries presented for comparison in FIG. 3 were from historical data previously published by our laboratory. The n-values for clonal relatedness include the following (FIG. 8b): from blood naïve cells of 5 donors (n=61, 24, 15, 14, and 24 sequences), from blood IgM memory cells of eight donors (n=28, 17, 27, 11, 23, 12, 29, and 20 VH gene sequences), and from blood IgG memory cells of six donors (n=23, 18, 18, 17, 22, and 21 sequences), tonsillar naïve B cells were analyzed from 8 tonsil donors (n=125, 32, 16, 22, 32, 23, 46, and 81 VH genes), tonsillar IgM germinal center (GC) and memory cells from 12 tonsil donors (n=50, 42, 35, 16, 60, 15, 50, 25, 39, 19, 55, and 58 VH genes), and tonsillar IgG GC or memory cells from 13 donors (n=113, 25, 14, 40, 12, 41, 11, 23, 18, 51, 15, 54, and 69 VH genes). For analysis of somatic hypermutation frequency only certain VH gene libraries with the highest quality sequences were considered. Background mutation rates were determined by analyses of a portion of the Ig-constant sequence cloned with each of the VDJ transcripts and that is not subjected to somatic hypermutation. Background mutations rates were insignificant. As each variable gene sequence also included a portion of the IgM of IgG constant region that is not targeted by physiological mutation we could verify that the sequences were of high quality. The n-values for analysis of somatic hypermutation include the following: 357 sequences of anti-influenza ASCs from 11 donors (by donor, n=63, 18, 33, 46, 49, 11, 36, 11, 30, 35, 25); For IgG GC and memory cells, 623 VH gene sequences were analyzed from 14 donors (by donor n=110, 37, 19, 28, 174, 40, 25, 15, 21, 18, 22, 24, 19, 71); for IgM GC and memory cells 638 VH gene sequences were analyzed from 17 donors (by donor, n=56, 158, 18, 91, 17, 10, 16, 30, 19, 28, 11, 36, 29, 13, 22, 20, 64); and for naïve cells 166 sequences from 6 donor (by donor, n=18, 42, 21, 34, 15, 36). Antibodies expressed from the clonal variants differing only by accumulated somatic mutations bound similarly to the vaccine virus strains and antigens and are included in the total enumerations but are not graphed.

Recombinant monoclonal antibody expression Following purification and digestion of the VH (digest: AgeI and SalI) or Vk (digest: AgeI and BsiWI) genes, the amplified cDNAs of the antibody variable genes from each single cell were cloned into expression vectors containing human IgG, or Igκ constant regions as previously described (FIG. 6b). Maxi prep plasmids (Qiagen) containing the heavy and light chain Ig genes were cotransfected into the 293A cell line using the Calcium Phosphate method. Transfected 293A cells were allowed to secrete antibodies in serum-free DMEM supplemented with 1% Nutridoma SP (Roche) for 4 to 5 days. Antibodies were purified using immobilized protein A beads (Pierce). Proper antibody expression and purity were verified by polyacrylamide gel electrophoresis, and purified antibody concentrations were determined using the EZQ Protein Quantization system (Molecular Probes). Naïve cell and IgG memory cell antibodies from unimmunized donors were produced previously in the laboratory.

ELISA to determine influenza binding affinities To screen for influenza binding ELISA, microtiter plates were coated with a cocktail of the vaccine strains totaling 8 HAU of total virus per well (2005/2006: A/New Caledonia/20/99,A/California/7/2004, and B/Shanghai/361/2002-like, 2006/2007: A/New Caledonia/20/99,A/Wisconsin/67/2005, and B/Malaysia/2506/2004). Each individual virus strain was then used in ELISA assays to characterize the affinity and specificity of antibodies reactive to the mixture. As described within the text some antibodies were also tested for binding to the actual vaccine by coating the plates with the various vaccines at a dilution of 1/20 in PBS. Influenza viruses were freshly grown in chicken eggs and purified by sucrose gradient centrifugation by standard methods23. Goat anti-human IgG (Goat anti-human I-peroxidase-conjugate (Jackson ImmunoResearch, West Grove, Pa.) was used to detect binding of the recombinant antibodies followed by development with horseradish peroxidase substrate (BioRad, Hercules, Calif.). Absorbencies were measured at OD415 on a microplate reader (Molecular Devices, Sunnyvale, Calif.). Antibody affinities (Kd or half maximum dissociation constants) were calculated by nonlinear regression analysis and SCATCHARD plots of influenza ELISA curves plotted from a dilution series of 8 concentrations of antibody ranging from 10 µg/ml to 0.125 ug/ml using the GraphPad Prism statistics software.

Viral Neutralization assays Influenza neutralizing activity was detected using MDCK cells and 100TCID50 (50% Tissue culture infectious doses) of A/Wisconsin/67/2005 or B/Shanghai/361/2002 based on the WHO manual. Briefly, the virus-antibody mixture was incubated with 100TCID50 at room temperature for 2 hrs prior to the monolayers of MDCK cells. The plate was incubated at 37° C. with 5% $CO_2$ and humidified atmosphere for 3-4 days. The cell cultures were then observed under inverted microscope and scored for viral Cytopathogenic effect.

Immunoprecipitation and Western Blot analyses For IP, 100 ul lysis Buffer (1% Triton X-100, 50 mM Tris-HCl-pH8.0, 150 mM NaCl, 1% Sodium Deoxycholate, 0.1% SDS) was mixed with 8 HAU of virus and incubated at RT for 30 min. Antibody was added to 10 ug/ml (1 µg of mAb). The antibody and viral lysate was incubated at 37° C. for 40-50 min. Protein A-Sepharose (Pierce) was prepared in Lysis buffer at a volume of 25 ul/sample. Protein A-Sepharose was incubated with the Ab-virus lysate at RT for 1 hr with constant agitation. The protein A-Sepharose was pelleted by centrifugation for 3 min at 3000 rpm and the precipitate washed with 400 ul of lysis buffer. The protein-A-Sepharose was again pelleted and washed with 400 ul of 20 mM Tris (pH7.5). The protein-A-Sepharose was again pelleted and then resuspended into 25 µl of Laemmli gel sample buffer (Bio-Rad). The samples were then boiled for 5 min at 95 C. The protein A was pelleted and 15-20 µl of supernatant was loaded onto 12% Tris-Glycine polyacrylamide gels. The gels were run in 1×TGS at 150V for 1 hr 30 min and then stained with syproorange (IX, Invitrogen) in 7.5% acetic acid for 45 min-1 hr. The gels were then destained with 7.5% acetic acid for 45 min. Gels were then read using a STORM840 system (Molecular Dynamics). For Western blots, virus (8 HAU) was diluted and boiled in denaturing/reducing sample buffer, then run on denaturing polyacrylamide gels (as above) followed by electrophoretic transfer to nitrocellulose membranes. The membranes were incubated with each Ab at 5 ug/ml and detected with HRP anti-human IgG (Jackson Immunoresearch) and developed with ECL plus reagent (GE health care). Membranes were analyzed using a STORM840 system (Molecular Dynamics).

What is claimed is:

1. A method for producing an antibody molecule that binds an antigen, the method comprising:
   (a) obtaining a sample of cells enriched for PBMC from a biological sample comprising antibody producing cells obtained from a mammal after exposure of the mammal to the antigen;
   (b) isolating a population of $CD19^{high}CD3^{neg}CD20^{low\ to\ neg}CD38^{high}CD27^{high}$ cells from the sample of cells enriched for PBMC based on expression of each of said markers,
   (c) isolating from a selected $CD19^{high}CD3^{neg}CD20^{low\ to\ neg}CD38^{high}CD27^{high}$ cell or progeny of the selected $CD19^{high}CD3^{neg}CD20^{low\ to\ neg}CD38^{high}CD27^{high}$ cell, a nucleic acid molecule encoding at least a portion of an antibody light chain expressed by the $CD19^{high}CD3^{neg}CD20^{low\ to\ neg}CD38^{high}CD27^{high}$ cell, wherein the portion of the antibody light chain comprises the variable domain, and a nucleic acid molecule encoding at least a portion of an antibody heavy chain expressed by the cell, wherein the portion of the antibody heavy chain comprises the variable domain, wherein the nucleic acid molecule that encodes the antibody light chain does not encode the antibody heavy chain;
   (d) transforming a recombinant cell with the nucleic acid sequence encoding at least a portion of the antibody light chain comprising the light chain variable domain and a nucleic acid sequence encoding at least a portion of the antibody heavy chain comprising the heavy chain variable domain, wherein the light chain variable domain and the heavy chain variable were paired in the selected cell; and
   (e) culturing the recombinant cell to produce an antibody molecule the binds the antigen.

2. The method of claim 1 wherein the mammal has been exposed to the antigen at least twice.

3. The method of claim 2 wherein the biological sample is collected from the mammal 3-10 days after the second exposure to the antigen.

4. The method of claim 3 wherein the biological sample is collected from the mammal 6-8 days after exposure of the mammal to the antigen.

5. The method of claim 1 wherein the mammal has been exposed only once to the antigen.

6. The method of claim 5 wherein the biological sample is collected from the mammal 10-18 days after the exposure to the antigen.

7. The method of claim 5 wherein the biological sample is collected from the mammal 12-16 days after the exposure to the antigen.

8. The method of claim 1 wherein the exposure to the antigen comprises immunization of the mammal with the antigen.

9. The method of claim 1 wherein the exposure to the antigen comprises accidental or deliberate infection of the mammal with an infectious agent comprising the antigen.

10. The method of claim 1 wherein the antigen is a self-antigen.

11. The method of claim 1 wherein the antigen is tumor antigen.

12. The method of claim 1 wherein step (b) comprises first isolating $CD19^{high}CD3^{neg}CD20^{low\ to\ neg}$ cells and then isolating $CD38^{high}CD27^{high}$ cells from the $CD19^{high}CD3^{neg}CD20^{low\ to\ neg}$ cells to produce the population of $CD19^{high}CD3^{neg}CD20^{low\ to\ neg}CD38^{high}CD27^{high}$ cells.

13. The method of claim 1, wherein the selected $CD19^{high}CD3^{neg}CD20^{low\ to\ neg}CD38^{high}CD27^{high}$ cell is $IgM^{neg}$, $IgD^{neg}$, $IgG^{pos}$.

14. The method of claim 1 wherein step (c) comprises single cell sorting.

15. The method of claim 1, wherein the mammal is immunized with a composition comprising the antigen prior to step (a).

16. The method of claim 9 wherein the infectious agent is a virus.

17. The method of claim 16 wherein the virus is selected from: an influenza virus, a herpes virus, a lenti virus, a poxvirus, and a coronavirus.

18. The method of claim 1 wherein at least 30% of the cells in the population of $CD19^{high}CD3^{neg}CD20^{low\ to\ neg}CD38^{high}CD27^{high}$ cells express an antibody that binds to the antigen.

19. A method for producing an antibody molecule that binds an influenza antigen, the method comprising:
   obtaining a sample of cells enriched for PBMC from a mammal after exposure of the mammal to an influenza antigen;

isolating a population of $CD19^{high}CD3^{neg}CD20^{low\ to\ neg}CD38^{high}CD27^{high}$ cells from the sample based on the expression of said markers isolating from a $CD19^{high}CD3^{neg}CD20^{low\ to\ neg}CD38^{high}CD27^{high}$ cell or progeny of the $CD19^{high}CD3^{neg}CD20^{low\ to\ neg}CD38^{high}CD27^{high}$ cell, a nucleic acid molecule encoding at least a portion of an antibody light chain expressed by the $CD19^{high}CD3^{neg}CD20^{low\ to\ neg}CD38^{high}CD27^{high}$ cell, wherein the portion of the antibody light chain comprises the variable domain, and a nucleic acid molecule encoding at least a portion of an antibody heavy chain expressed by the cell, wherein the portion of the antibody heavy chain comprises the variable domain, wherein the nucleic acid molecule that encodes the antibody light chain does not encode the antibody heavy chain;

transforming a recombinant host cell with the nucleic acid sequence encoding at least a portion of the antibody light chain comprising the light chain variable domain and the nucleic acid sequence encoding at least a portion of the antibody heavy chain comprising the heavy chain variable domain, wherein the light chain variable domain and the heavy chain variable domain were paired in the selected cell; and culturing the recombinant cell to produce an antibody molecule that binds the influenza antigen.

20. The method of claim 19, wherein the influenza antigen is hemagglutinin.

21. The method of claim 19, wherein the influenza antigen is neuraminidase.

22. The method of claim 19, wherein the mammal has been exposed to the antigen at least twice.

23. The method of claim 22 wherein the biological sample is collected from the mammal 3-10 days after the second exposure to the antigen.

24. The method of claim 23, wherein the biological sample is collected from the mammal 6-8 days after exposure of the mammal to the antigen.

25. The method of claim 19, wherein the mammal has been exposed only once to the antigen.

26. The method of claim 25, wherein the biological sample is collected from the mammal 10-18 days after the exposure to the antigen.

27. The method of claim 26, wherein the biological sample is collected from the mammal 12-16 days after the exposure to the antigen.

* * * * *

UNITED STATES PATENT AND TRADEMARK OFFICE
CERTIFICATE OF CORRECTION

PATENT NO. : 8,563,305 B2
APPLICATION NO. : 12/433832
DATED : October 22, 2013
INVENTOR(S) : Ahmed et al.

It is certified that error appears in the above-identified patent and that said Letters Patent is hereby corrected as shown below:

In the Specification:

Column 1, line 6, "grant no. AI057266" should read --grant nos. AI057266, AI050025, and HHSN266200500026C--.

Column 2, line 31, "Thus, and improved" should read --Thus, improved--.

Column 5, line 49, "The viruses include Abelson murine leukemia virus, Retroviridae" should read --The viruses include:

Abelson murine leukemia virus, Retroviridae--.

Column 6, line 53, "Elephantid" should read --Elephant--.

Column 6, line 56, "Nerpesviridae" should read --Herpesviridae--.

Column 7, line 46, "Guinea pig t, vope C oncovirus" should read --Guinea pig, type Concovirus--.

Column 13, line 34, "CD201$^{ow}$," should read --CD20$^{low}$--.

Column 18, Table 1, "5' AgeI Vκ 10-43/1-8" should read --5' AgeI Vκ 1D-43/1-8--.

Column 18, Table 1, "5' Age Vκ 3-11/30-11" should read --5' Age Vκ 3-11/3D-11--.

Column 19, Table 1-continued, "5' Age Vκ 3-15/30-15" should read --5' Age Vκ 3-15/3D-15--.

Column 19, Table 1-continued, "5' Age Vκ 3-15/30-20" should read --5' Age Vκ 3-15/3D-20--.

Column 19, Table 1-continued, "AgeI Vλ 6" should read --5' AgeI Vλ 6--.

Column 19, Table 1-continued, "3' SoII JH 1/2/4/5" should read --3' Sa/I JH 1/2/4/5--.

Column 19, Table 1-continued, "3' SoII JH 3" should read --3' Sa/I JH 3--.

Column 21, Table 1-continued, "3' SoII JH 6" should read --3' Sa/I JH 6--.

Signed and Sealed this
Seventeenth Day of June, 2014

Michelle K. Lee
*Deputy Director of the United States Patent and Trademark Office*

CERTIFICATE OF CORRECTION (continued)
U.S. Pat. No. 8,563,305 B2

Column 24, line 30, "3' SaII JH" should read --3' Sa/I JH--.

Column 28, line 4, "Basal media An" should read

--Basal media.

An--.

Column 33, line 10, "described27." should read --described.--.

Column 33, line 27, "and cell sorting Flow" should read --and cell sorting. Flow--.

Column 33, line 55, "or IgD+CD27-" should read --IgD$^+$CD27$^-$--.

Column 33, line 58, "genes Single" should read --genes: Single--.